United States Patent
Sengupta et al.

(10) Patent No.: US 9,024,021 B2
(45) Date of Patent: May 5, 2015

(54) DIARYLACETYLENE HYDRAZIDE CONTAINING TYROSINE KINASE INHIBITORS

(75) Inventors: Prabal Sengupta, Baroda (IN); Hemant Ashvinbhai Chokshi, Baroda (IN); Chetan Surjitsingh Puri, Baroda (IN); Sabbirhusen Yusufbhai Chimanwala, Baroda (IN); Varun Anilkumar Mehta, Baroda (IN); Dipali Manubhai Desai, Baroda (IN); Trinadha Rao Chitturi, Baroda (IN); Rajamannar Thennati, Baroda (IN)

(73) Assignee: Sun Pharma Advanced Research Company Ltd., Mumbai (IN)

( * ) Notice: Subject to any disclaimer, the term of this patent is extended or adjusted under 35 U.S.C. 154(b) by 0 days.

(21) Appl. No.: 13/980,108

(22) PCT Filed: Jan. 23, 2012

(86) PCT No.: PCT/GB2012/050132
§ 371 (c)(1),
(2), (4) Date: Jul. 17, 2013

(87) PCT Pub. No.: WO2012/098416
PCT Pub. Date: Jul. 26, 2012

(65) Prior Publication Data
US 2013/0296557 A1  Nov. 7, 2013

(30) Foreign Application Priority Data
Jan. 21, 2011  (IN) .......................... 184/MUM/2011

(51) Int. Cl.
| | | |
|---|---|---|
| C07D 487/04 | (2006.01) |
| C07D 215/14 | (2006.01) |
| C07D 241/40 | (2006.01) |
| C07D 213/56 | (2006.01) |
| C07D 215/12 | (2006.01) |
| C07D 231/12 | (2006.01) |
| C07D 239/74 | (2006.01) |
| C07D 277/64 | (2006.01) |
| C07D 401/06 | (2006.01) |
| C07D 401/12 | (2006.01) |
| C07D 409/06 | (2006.01) |
| C07D 417/06 | (2006.01) |
| C07D 471/04 | (2006.01) |
| C07C 243/38 | (2006.01) |

(52) U.S. Cl.
CPC ............ *C07D 241/40* (2013.01); *C07D 213/56* (2013.01); *C07D 215/12* (2013.01); *C07D 231/12* (2013.01); *C07D 239/74* (2013.01); *C07D 277/64* (2013.01); *C07D 401/06* (2013.01); *C07D 401/12* (2013.01); *C07D 409/06* (2013.01); *C07D 417/06* (2013.01); *C07D 471/04* (2013.01); *C07D 487/04* (2013.01); *C07C 243/38* (2013.01); *C07D 215/14* (2013.01)

(58) Field of Classification Search
None
See application file for complete search history.

(56) References Cited

FOREIGN PATENT DOCUMENTS

| EP | 1 314 723 A1 | 5/2003 |
| WO | 2005/094822 A1 | 10/2005 |
| WO | 2007/075869 A2 | 7/2007 |

OTHER PUBLICATIONS

International Search Report for PCT/GB2012/050132 dated Feb. 29, 2012.
Compound Summary for CID 1350168, PubChem Open Chemistry Database, U.S. National Library of Medicine, National Center for Biotechnology Information, pp. 1-11; printed Dec. 11, 2014; http://pubchem.ncbi.nlm.nih.gov/compound/1350168.

*Primary Examiner* — Timothy R Rozof
(74) *Attorney, Agent, or Firm* — Sughrue Mion, PLLC

(57) ABSTRACT

The present invention relates to novel diarylacetylene hydrazide compounds of formula (I) or pharmaceutically acceptable salt thereof, as tyrosine kinase inhibitors, the process for their preparation, and to the use of the compounds of formula (I) in the preparation of pharmaceutical compositions for the therapeutic treatment of disorders related to tyrosine kinases, in warm-blooded animals.

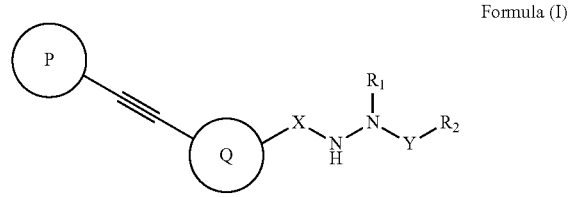

Formula (I)

10 Claims, No Drawings

DIARYLACETYLENE HYDRAZIDE CONTAINING TYROSINE KINASE INHIBITORS

RELATED APPLICATION

This application claims the benefit of Indian Patent Application No. 184/MUM/2011 filed on Jan. 21, 2011 which is hereby incorporated by reference.

The present invention relates to novel diarylacetylene hydrazides as tyrosine kinase inhibitors, process of preparation thereof and to the use of the compounds in the preparation of pharmaceutical compositions for the therapeutic treatment of disorders related to tyrosine kinases, in warm-blooded animals.

BACKGROUND OF THE INVENTION

Protein tyrosine kinases are currently recognized as important molecular targets for drug development in the treatment of several disorders, particularly in the treatment of proliferative disorders. Dysregulation of tyrosine kinase activity has emerged as a major mechanism by which cancer cells evade normal physiological constraints on growth, proliferation and survival.

Tyrosine kinases (TKs) are enzymes that catalyze the transfer of phosphate from ATP to tyrosine residues in polypeptides. The human genome contains about 90 TK and 43 TK-like genes, the products of which control a wide variety of cellular events including cellular proliferation, survival, differentiation, function and motility.

TKs are divided into two main classes viz. receptor TKs and non-receptor TKs. Activities of both types of TKs are under tight control so that non-proliferating cells have very low levels of tyrosyl phosphorylated proteins. Receptor TKs become activated when ligand binds to the extracellular domain resulting in receptor oligomerization, disruption of the autoinhibitory juxtamembrane interaction and autophosphorylation of a regulatory tyrosine within the activation loop of the kinase. After activation, autophosphorylation generates binding sites for signaling proteins, recruiting them to the membrane and activating multiple signaling pathways.

The non-receptor TKs such as c-Abl, are maintained in an inactive state by cellular inhibitor proteins, lipids and through intramolecular autoinhibition. Non-receptor TKs are activated by diverse intracellular signals through dissociation of inhibitors, by recruitment to transmembrane receptors (causing oligomerization and autophosphorylation) and through transphosphorylation by other kinases. TK signaling is terminated in part through the action of tyrosine phosphatases that hydrolyze tyrosyl phosphates and by the induction of inhibitory molecules.

Dysregulation of TK activity arising out of mutation, overexpression or dysfunctional autoregulatory mechanisms has been implicated in many diseases including cancer. Given the multiple levels of regulation of TKs, it is not surprising that TKs are dysregulated in cancer cells by several ways. A common mechanism of TK activation in hematological cancers is the fusion of a receptor or non-receptor TK with a partner protein, usually as a consequence of a balanced chromosomal translocation. A primary example of this mechanism is Bcr-Abl, the non-receptor fusion TK in CML, in which a tetramerization domain in Bcr overcomes autoinhibition of Abl catalytic activity through oligomerization and autophosphorylation. With some receptor TKs, absence of the juxtamembrane inhibitory domain in the fusion protein contributes to activation. A second important mechanism of TK dysregulation is a mutation that disrupts autoregulation of the kinase. Mutations in the Fms-like tyrosine kinase 3 (FLT3) receptor in acute myeloid leukemia (AML) render this TK active in the absence of ligand; in another example, small deletions and point mutations in the kinase domain of epidermal growth factor receptor (EGFR) in a subset of non-small-cell lung cancers increase the sensitivity of the receptor to its ligand and alter receptor signaling. A third mechanism of TK dysregulation is increased or aberrant expression of a receptor TK, its ligand, or both. Examples include overexpression of the receptor TK ErbB2 (HER-2/neu) in breast cancer and overexpression of a mutant form of platelet-derived growth factor (PDGF), a receptor TK ligand, in dermatofibrosarcoma protuberans with t(11;17). Lastly, increased TK activity can result from a decrease in factors that limit TK activity, such as impaired tyrosine phosphatase activity or decreased expression of TK inhibitor proteins. Aberrant TK activation can increase the survival, proliferation and cytotoxic drug resistance of malignant cells; in tumors it can increase angiogenesis, invasiveness and metastatic potential.

The TK family of enzymes has emerged as an important class of targets for therapeutic intervention. TKs can be inhibited pharmacologically through multiple mechanisms. One of the key focus areas in anti-TK drug discovery is the design and development of small molecules that can directly inhibit the catalytic activity of the kinase by interfering with the binding of ATP or substrates. An important advantage of TK-directed therapy is the possibility to perform pharmacodynamic studies that correlate inhibition of the targeted TK in cancer cells with clinical responses to the drug.

The dysregulated TK in the hematological cancers is Bcr-Abl which has been implicated as the direct cause of CML. Imatinib mesylate (Gleevec®), a 2-phenylaminopyrimidine compound by virtue of its inhibition of several TKs viz. Abl, Abl-related gene product (ARG), c-Kit and PDGF receptor (PDGFR) has demonstrated remarkable clinical efficacy in CML. It induces complete hematological and cytogenetic remissions in most patients with chronic-phase, however is much less effective in the accelerated and blast-crisis phases of the disease. It is the first TK inhibitor to be approved as first line monotherapy and has revolutionized the treatment for CML. Recently it has been shown that imatinib mesylate prevents β-cell apoptosis under conditions of β-cell stress (PNAS, 2008, vol. 105, 18895-18900). This, together with the observation that improvements in type II diabetes has been noted in patients on imatinib therapy, leads to the hypothesis that kinase inhibitors may prove to be beneficial in the treatment of diabetes. The tyrosine kinase EGFR has been targeted with small molecule inhibitors such as Tarceva® and Iressa® for the treatment of patients with non-small cell lung carcinoma (NSCLC). Sutent® is approved for the treatment of certain tumors because of its multi-modal action on the tyrosine kinases including the vascular endothelial growth factor receptor (VEGFR), Kit and PDGFR. Inhibition of other kinases with small molecule inhibitors include the tyrosine kinase FLT3 that is expressed on blasts in most cases of acute myeloid leukemia (AML), the tyrosine kinases FGFR1, FGFR3, c-FMS, JAK and SYK in a range of malignant hematological disorders and ALK, c-Met and RET in a host of solid tumors.

Inhibiting TKs with ATP-competitive kinase inhibitors block the enzymatic activity of the kinases. Often treatment therapies result in drug resistance over a period. Quite often, drug resistance is largely on account of mutations that occur to prevent the pressures exerted by drug binding. Thus, despite success with Gleevec® to treat CML through inhibition of the oncogene Bcr-abl, clinical resistance to the drug has been observed. Of the multiple mechanisms of drug resistance, mutations of the Bcr-Abl kinase have been particularly problematic, with 50-90% of the resistance to Gleevec® arising from mutations in the kinase domain. Over 22 mutations have been reported to date, some of the most common being G250E, Q252H, Y253F/H, E255K/V, T315A/I, F317L/V, M351T, F359V and H396R.

The second generation agents such as nilotinib (Tasigna®) and dasatinib (Sprycel®) are able to inhibit a large number of clinically relevant mutations. However, neither of these inhibit the T315I mutation (also known as the gatekeeper mutation), although this mutation is the largest singly occurring mutation to the current standard of care for CML viz. Gleevec®. Mutation of the gatekeeper residue enables the protein to bind ATP and continue to function. At the same time, Gleevec® is selectively rejected since it makes use of a hydrophobic pocket close to the ATP binding site, which ATP does not utilize. In fact, almost all small molecule inhibitors that are ATP-competitive utilize this hydrophobic pocket to attain much higher potency over ATP, Gleevec® is no exception. It is therefore not surprising that the gatekeeper and its mutation across numerous kinases are well known since most small molecule inhibitors of kinases are ATP competitive.

The Src family which consists of at least eight members (Src, Fyn, Lyn, Yes, Lck, Fgr, Hck and Blk) that participate in a variety of signaling pathways represents the major family of cytoplasmic protein tyrosine kinases. The prototypical member of this tyrosine kinase family is Src, which is involved in proliferation and migration responses in many cell types. Src activity has been shown to be elevated in different cancers, e.g. breast, colon, pancreatic and liver tumors. Highly increased Src activity is also associated with metastasis and poor prognosis. Antisense Src message impedes growth of colon tumor cells in nude mice, suggesting that Src inhibitors could slow tumor growth. Furthermore, in addition to its role in cell proliferation, Src also acts in stress response pathways, including the hypoxia response.

In addition, Src family kinases such as Lyn and Src are important in the Fc epsilon receptor induced degranulation of mast cells and basophils that plays an important role in asthma, allergic rhinitis and other allergic disease.

The lymphocyte-specific kinase (Lck), belonging to the Src family of tyrosine kinases, is expressed in T cells and natural killer (NK) cells and is responsible for the activation of and signaling through the T-cell receptor. This activation cascade results in the upregulation of inflammatory cytokines such as IL-2 and interferon (IFN)-γ, and ultimately in the activation and proliferation of T lymphocytes to generate an immune response. Inhibition of Lck is therefore likely to elicit an immunosuppressive effect that could be useful in the treatment of T-cell-mediated diseases like rheumatoid arthritis, inflammatory bowel disease, psoriasis, and organ graft rejection.

Classical tyrosine kinase inhibitors, which are predominantly the Bcr-Abl kinase inhibitors that are currently in clinical use, are described in the following patent literature:
U.S. Pat. No. 5,521,184 (the '184 patent): Exemplifies 4-[(Methyl-1-piperazinyl)methyl]-N-[4-methyl-3-[[4-(3-pyridinyl)-2-pyrimidinyl]amino]-phenyl]benzamide methanesulfonate (Imatinib mesylate, Gleevec®)
U.S. Pat. No. 7,169,791 (the '791 patent): Exemplifies 4-Methyl-N-[3-(4-methyl-imidazol-1-yl)-5-trifluoromethyl-phenyl]-3-(4-pyridin-3-yl-pyrimidin-2-ylamino)-benzamide (Nilotinib, Tasigna®)
U.S. Pat. No. 6,596,746 (the '746 patent): Exemplifies N-(2-chloro-6-methylphenyl)-2-(6-(4-(2-hydroxyethyl)piperazin-1-yl)-2-methylpyrimidin-4-ylamino)thiazole-5-carboxamide (Dasatinib, Sprycel®)

While the second generation TK inhibitors in clinic viz. nilotinib and dasatinib have provided additional treatment option to patients who have developed resistance to imatinib, there are certain shortcomings with regard to their side effects. Particularly in the case of dasatinib, the increased potency may be associated with untoward off-target toxicities, which probably relate to their inhibitory activity against a broader range of protein kinases such as Kit, PDGFR and ephrin receptor (EphA2) tyrosine kinases which are directly implicated in haematopoiesis, control of tissue interstitial-fluid pressure and angiogenesis. These effects may provide the physiological explanation for some of the toxicities associated with dasatinib therapy such as myelosuppression and pleural effusion. Besides, treatment with highly potent Abl kinase inhibition has potential for the development of cardiotoxicity in patients with CML.

Although the second generation TK inhibitors in clinic provide treatment alternatives for patients who develop resistance to imatinib therapy, the prognosis for the patients having T315I mutation is not good since none of these currently marketed therapies are effective. There is thus an unmet medical need with regard to treatment of patients having the T315I mutation. Omacetaxine (homoharringtonine) is currently being evaluated by the FDA for CML patients with T315I. However, it is an intravenous drug with a non-specific mechanism of action. Other drug candidates in clinical phase include the Deciphera compound DCC-2036 (PCT Publication No. WO 2008/046003) and the Ariad compound AP24534 (Ponatinib, PCT Publication No. WO 2007/075869).

There is thus a need for newer selective TK inhibitors which are orally active, safer than existing therapies particularly with regard to decrease in cardiac toxicity associated with hERG/QT prolongation, and efficacious against the kinase mutations, including the T315I mutant for which there is currently no approved therapy. The current invention describes novel diarylacetylene hydrazide containing compounds which are potent inhibitors of Abl tyrosine kinase and their mutated forms, including the T315I mutant.

SUMMARY OF THE INVENTION

The present invention relates to compounds of formula (I),

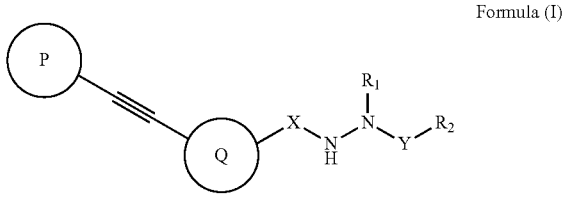

Formula (I)

or pharmaceutically acceptable salt thereof, wherein;
ring P and ring Q are independently selected from an aryl ring having 6 to 14 carbon atoms, or a 5 to 14 membered heteroaryl ring containing one to four hetero atoms each independently selected from O, S and N, optionally substituted by one or more identical or different radicals $R_3$, with a proviso that when ring Q is pyridyl then ring P is heteroaryl;
$R_1$ and $R_2$ are independently selected from the group consisting of hydrogen, —$C_{1-8}$-alkyl, —$C_{2-10}$-alkenyl, —$C_{2-12}$-alkynyl, —$C_{3-12}$-cycloalkylalkyl, —$C_{4-12}$-cycloalkylalkyl, —$C_{3-12}$-cycloalkenyl, aryl, heteroaryl, arylalkyl and a heteroarylalkyl radical, wherein the aryl ring contains 6 to 14 carbon atoms, and the heteroaryl ring contains 5 to 14 membered ring system with one to four hetero atoms each independently selected from O, S and N, and are optionally substituted by one or more identical or different radicals $R_3$;

X and Y are independently selected from the group consisting of C=O and C=S;

$R_3$ is selected from the group consisting of halogen, —OH, —CN, —NO$_2$, —N$_3$, —C$_{1-8}$-alkyl, —C$_{3-12}$-cycloalkyl, —(C$_{1-8}$-alkyl)-C$_{3-12}$-cycloalkyl, -heterocycloalkyl containing 3 to 12 rings atoms having one or two hetero atoms each independently selected from O, S and N, —(C$_{1-8}$-alkyl)-heterocycloalkyl containing 3 to 12 rings atoms having one or two hetero atoms each independently selected from O, S and N, —O—C$_{1-8}$-alkyl, —O—C$_{3-12}$-cycloalkyl, —O-aryl, —O-heteroaryl, —C$_{1-8}$ alkyl-O—C$_{1-8}$ alkyl, —O—C$_{1-8}$ alkyl-O—C$_{1-8}$ alkyl, —O—C$_{1-8}$ alkyl-NH(C$_{1-8}$ alkyl), —O—C$_{1-8}$ alkyl-N(C$_{1-8}$ alkyl)$_2$, —O—C$_{1-8}$ alkyl-(heteroaryl), —C(O)—C$_{1-8}$ alkyl, —COOH, —C(O)NH$_2$, —C(O)NH—C$_{1-8}$ alkyl, —C(O)N(C$_{1-8}$ alkyl)$_2$, —C(O)O—C$_{1-8}$ alkyl, —C$_{1-8}$ haloalkyl, —C$_{2-10}$ alkenyl, —C$_{2-12}$ alkynyl, —OC(O)—NH$_2$, —OC(O)—NH(C$_{1-8}$ alkyl), —OC(O)—N(C$_{1-8}$ alkyl)$_2$, —NH$_2$, —NH(C$_{1-8}$ alkyl), —N(C$_{1-8}$ alkyl)$_2$, —NH—SO$_2$—C$_{1-8}$ alkyl, —N(C$_{1-8}$ alkyl)-SO$_2$—C$_{1-8}$ alkyl, —NH—C(O)—(C$_{1-8}$ alkyl), —N(C$_{1-8}$ alkyl)-C(O)—(C$_{1-8}$ alkyl), —NH—C(O)O—C$_{1-8}$ alkyl, —N(C$_{1-8}$ alkyl)-C(O)O—C$_{1-8}$ alkyl, —NH—C(O)—NH$_2$, —NH—C(O)—NH(C$_{1-8}$ alkyl), —N(C$_{1-8}$ alkyl)-C(O)—NH(C$_{1-8}$ alkyl), —N(C$_{1-8}$ alkyl)-C(O)—N(C$_{1-8}$ alkyl)$_2$, —NH—C(O)—NH—SO$_2$—C$_{1-8}$ alkyl, —N(C$_{1-8}$ alkyl)-C(O)—NHSO$_2$—C$_{1-8}$ alkyl, —N(C$_{1-8}$ alkyl)-C(O)—N(C$_{1-8}$ alkyl)-SO$_2$—C$_{1-8}$ alkyl, —S—C$_{1-8}$ alkyl, —S(O)—C$_{1-8}$ alkyl, —SO$_2$—C$_{1-8}$ alkyl, —S-aryl, —S(O)-aryl, SO$_2$-aryl, —SO$_2$NH$_2$, —SO$_2$NH—(C$_{1-8}$ alkyl), —SO$_2$N(C$_{1-8}$ alkyl)$_2$; -aryl, —(C$_{1-4}$-alkyl)-aryl, heteroaryl or —(C$_{1-4}$-alkyl)-heteroaryl group, wherein the aryl ring contains 6 to 14 carbon atoms, and the heteroaryl ring contains 5 to 14 membered ring system with one to four hetero atoms each independently selected from O, S and N, wherein each of the aforementioned $R_3$ groups may be optionally substituted with a single group selected from the group consisting of: C$_{1-4}$-alkyl, C$_{1-4}$-alkoxy, C$_{1-4}$-haloalkyl, —OH, —COOH, —CN, —NO$_2$, halo, —NH$_2$ and —SO$_2$NH$_2$.

The invention also provides the use of compound of formula (I) or salt or N-oxides thereof for the preparation of pharmaceutical composition comprising compound of formula (I) or N-oxide thereof and a pharmaceutically acceptable carrier, diluent or excipient thereof.

Further the present invention also provides a method for treatment of disorders dependent on tyrosine kinases comprising administering to a mammal in need of such treatment an effective amount of compound of formula (I) or salt or N-oxides thereof.

DETAILED DESCRIPTION OF THE INVENTION

The present invention relates to compounds of formula (I),

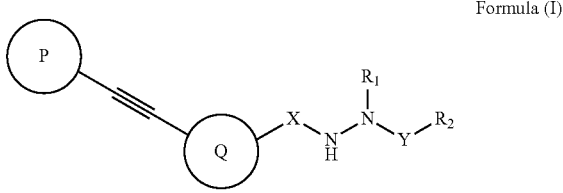

Formula (I)

or pharmaceutically acceptable salt thereof, wherein;

ring P and ring Q are independently selected from an aryl ring having 6 to 14 carbon atoms, or a 5 to 14 membered heteroaryl ring containing one to four hetero atoms each independently selected from O, S and N, optionally substituted by one or more identical or different radicals $R_3$, with a proviso that when ring Q is pyridyl then ring P is heteroaryl;

$R_1$ and $R_2$ are independently selected from the group consisting of hydrogen, —C$_{1-8}$-alkyl, —C$_{2-10}$-alkenyl, —C$_{2-12}$-alkynyl, —C$_{3-12}$-cycloalkyl, —C$_{4-12}$-cycloalkylalkyl, —C$_{3-12}$-cycloalkenyl, aryl, heteroaryl, arylalkyl and a heteroarylalkyl radical, wherein the aryl ring contains 6 to 14 carbon atoms, and the heteroaryl ring contains 5 to 14 membered ring system with one to four hetero atoms each independently selected from O, S and N, and are optionally substituted by one or more identical or different radicals $R_3$;

X and Y are independently selected from the group consisting of C=O and C=S;

$R_3$ is selected from the group consisting of halogen, —OH, —CN, —NO$_2$, —N$_3$, —C$_{1-8}$-alkyl, —C$_{3-12}$-cycloalkyl, —(C$_{1-8}$-alkyl)-C$_{3-12}$-cycloalkyl, -heterocycloalkyl containing 3 to 12 rings atoms having one or two hetero atoms each independently selected from O, S and N, —(C$_{1-8}$-alkyl)-heterocycloalkyl containing 3 to 12 rings atoms having one or two hetero atoms each independently selected from O, S and N, —O—C$_{1-8}$-alkyl, —O—C$_{3-12}$-cycloalkyl, —O-aryl, —O-heteroaryl, —C$_{1-8}$ alkyl-O—C$_{1-8}$ alkyl, —O—C$_{1-8}$ alkyl-O—C$_{1-8}$ alkyl, —O—C$_{1-8}$ alkyl-NH(C$_{1-8}$ alkyl), —O—C$_{1-8}$ alkyl-N(C$_{1-8}$ alkyl)$_2$, —O—C$_{1-8}$ alkyl-(heteroaryl), —C(O)—C$_{1-8}$ alkyl, —COOH, —C(O)NH$_2$, —C(O)NH—C$_{1-8}$ alkyl, —C(O)N(C$_{1-8}$ alkyl)$_2$, —C(O)O—C$_{1-8}$ alkyl, —C$_{1-8}$ haloalkyl, —C$_{2-10}$ alkenyl, —C$_{2-12}$ alkynyl, —OC(O)—NH$_2$, —OC(O)—NH(C$_{1-8}$ alkyl), —OC(O)—N(C$_{1-8}$ alkyl)$_2$, —NH$_2$, —NH(C$_{1-8}$ alkyl), —N(C$_{1-8}$ alkyl)$_2$, —NH—SO$_2$—C$_{1-8}$ alkyl, —N(C$_{1-8}$ alkyl)-SO$_2$—C$_{1-8}$ alkyl, —NH—C(O)—(C$_{1-8}$ alkyl), —N(C$_{1-8}$ alkyl)-C(O)—(C$_{1-8}$ alkyl), —NH—C(O)O—C$_{1-8}$ alkyl, —N(C$_{1-8}$ alkyl)-C(O)O—C$_{1-8}$ alkyl, —NH—C(O)—NH$_2$, —NH—C(O)—NH(C$_{1-8}$ alkyl), —N(C$_{1-8}$ alkyl)-C(O)—NH(C$_{1-8}$ alkyl), —N(C$_{1-8}$ alkyl)-C(O)—N(C$_{1-8}$ alkyl)$_2$, —NH—C(O)—NH—SO$_2$—C$_{1-8}$ alkyl, —N(C$_{1-8}$ alkyl)-C(O)—NHSO$_2$—C$_{1-8}$ alkyl, —N(C$_{1-8}$ alkyl)-C(O)—N(C$_{1-8}$ alkyl)-SO$_2$—C$_{1-8}$ alkyl, —S—C$_{1-8}$ alkyl, —S(O)—C$_{1-8}$ alkyl, —SO$_2$—C$_{1-8}$ alkyl, —S-aryl, —S(O)-aryl, SO$_2$-aryl, —SO$_2$NH$_2$, —SO$_2$NH—(C$_{1-8}$ alkyl), —SO$_2$N(C$_{1-8}$ alkyl)$_2$; -aryl, —(C$_{1-4}$-alkyl)-aryl, heteroaryl or —(C$_{1-4}$-alkyl)-heteroaryl group, wherein the aryl ring contains 6 to 14 carbon atoms, and the heteroaryl ring contains 5 to 14 membered ring system with one to four hetero atoms each independently selected from O, S and N, wherein each of the aforementioned $R_3$ groups may be optionally substituted with a single group selected from the group consisting of: C$_{1-4}$-alkyl, C$_{1-4}$-alkoxy, C$_{1-4}$-haloalkyl, —OH, —COOH, —CN, —NO$_2$, halo, —NH$_2$ and —SO$_2$NH$_2$.

The invention also provides a pharmaceutical composition comprising a compound of formula (I), as defined above, and a pharmaceutically acceptable carrier.

Additionally provided is a method of treating a condition associated with at least one tyrosine kinase enzyme comprising administering to a mammalian species in need of such treatment an effective amount of a compound of formula (I), as defined above.

The following are definitions of the terms used in this specification. The initial definition provided for a group or term herein applies to that group or term throughout the present specification, individually or as part of another group, unless otherwise indicated.

The general terms used hereinbefore and hereinafter preferably have within the context of this disclosure the following meanings, unless otherwise indicated.

The term "$C_{1-8}$-alkyl" refers to an alkyl chain, linear or branched having 1 to 8 carbon atoms, both inclusive. e.g., methyl, ethyl, n-propyl, 1-methylethyl (isopropyl), n-butyl, n-pentyl, and 1,1-dimethylethyl (t-butyl). Unless set forth or recited to the contrary, all alkyl groups described or claimed herein may be substituted or unsubstituted.

The term "$C_{2-10}$-alkenyl" refers to a hydrocarbon chain containing from 2 to 10 carbon atoms, both inclusive and including at least one carbon-carbon double bond which is not in the 1 position, and may have (E) or (Z) configuration. Non-limiting examples of alkenyl groups include 2-propenyl (allyl), 2-methyl-2-propenyl, and (Z)-2-butenyl. Unless set forth or recited to the contrary, all alkenyl groups described or claimed herein may be straight chain or branched, substituted or unsubstituted.

The term "$C_{2-12}$-alkynyl" refers to a hydrocarbyl radical having at least one carbon-carbon triple bond which is not in the 1 position, and having 2 to about 12 carbon atoms, both inclusive (with radicals having 2 to about 10 carbon atoms. Non-limiting examples of alkynyl groups include 2-propynyl and 3-butynyl. Unless set forth or recited to the contrary, all alkynyl groups described or claimed herein may be straight chain or branched, substituted or unsubstituted.

The term "alkoxy" or "—O—$C_{1-8}$ alkyl" denotes an alkyl group attached via an oxygen linkage to the rest of the molecule. Representative examples of such groups are —$OCH_3$ and —$OC_2H_5$. Unless set forth or recited to the contrary, all alkoxy groups described or claimed herein may be straight chain or branched, substituted or unsubstituted.

The terms "halogen" or "halo" means fluorine (fluoro), chlorine (chloro), bromine (bromo) or iodine (iodo).

Similarly, "haloalkyl" or "haloalkoxy" refers to an —$C_{1-8}$-alkyl or alkoxy group substituted with one or more halogen atoms.

The term "$C_{3-12}$-cycloalkyl" denotes a non-aromatic mono-, or multicyclic ring system of 3 to about 12 carbon atoms. Monocyclic rings include include, but are not limited to cylcopropyl, cyclobutyl, cyclopentyl and cyclohexyl. Examples of simple multicyclic cycloalkyl groups include perhydronapththyl, perhydroindenyl etc; bridged multicyclic groups include adamantyl and norbornyl etc, and spriromulticyclic groups for e.g., spiro(4,4)non-2-yl. Unless set forth or recited to the contrary, all cycloalkyl groups described or claimed herein may be substituted or unsubstituted.

The term "$C_{4-12}$-cycloalkylalkyl" refers to a cyclic ring-containing radical having 4 to about 12 carbon atoms directly attached to an alkyl group. The cycloalkylalkyl group may be attached to the main structure at any carbon atom in the alkyl group that results in the creation of a stable structure. Non-limiting examples of such groups include cyclopropylmethyl, cyclobutylethyl and cyclopentylethyl. Unless set forth or recited to the contrary, all cycloalkylalkyl groups described or claimed herein may be substituted or unsubstituted.

The term "$C_{3-12}$-cycloalkenyl" refers to a cyclic ring-containing radical having 3 to about 12 carbon atoms with at least one carbon-carbon double bond which is not in the 1 position, such as cyclopropenyl, cyclobutenyl and cyclopentenyl. Unless set forth or recited to the contrary, all cycloalkenyl groups described or claimed herein may be substituted or unsubstituted.

The term "heterocycloalkyl containing 3 to 12 rings atoms having one or two hetero atoms each independently selected from O, S and N" denotes a non-aromatic mono-, or multicyclic ring system of 3 to about 12 ring atoms. Monocyclic rings include, but are not limited to piperidine, tetrahydro-2H-pyran, tetrahydro-2H-thiopyran, piperazine, morpholine, thiomorpholine, hexahydropyrimidine, 1,3-oxazine and 1,3-thiazinanecylcopropyl. Unless set forth or recited to the contrary, all heterocycloalkyl containing 3 to 12 rings atoms having one or two hetero atoms each independently selected from O, S and N described or claimed herein may be substituted or unsubstituted.

The term "aryl" refers to an aromatic radical having 6 to 14 carbon atoms, including monocyclic, bicyclic and tricyclic aromatic systems such as phenyl, naphthyl, tetrahydronapthyl, indanyl and biphenyl. Unless set forth or recited to the contrary, all aryl groups described or claimed herein may be substituted or unsubstituted.

The term "heteroaryl" unless otherwise specified refers to substituted or unsubstituted 5 to 14 membered aromatic heterocyclic ring radicals with one or more heteroatom(s) independently selected from N, O or S. The heteroaryl may be a mono-, bi- or tricyclic ring system. The heteroaryl ring radical may be attached to the main structure at any heteroatom or carbon atom that results in the creation of a stable structure. Examples of such heteroaryl ring radicals include, but are not limited to oxazolyl, isoxazolyl, imidazolyl, furyl, indolyl, isoindolyl, pyrrolyl, triazolyl, triazinyl, tetrazoyl, thienyl, thiazolyl, isothiazolyl, pyridyl, pyrimidinyl, pyrazinyl, pyridazinyl, benzofuranyl, benzothiazolyl, benzoxazolyl, benzimidazolyl, benzothienyl, benzopyranyl, carbazolyl, quinolinyl, isoquinolinyl, quinazolinyl, cinnolinyl, naphthyridinyl, pteridinyl, purinyl, quinoxalinyl, quinolinyl, isoquinolinyl, thiadiazolyl, indolizinyl, acridinyl, phenazinyl, imidazo[1,2-a]pyridyl, imidazo[1,2-a]pyridine and phthalazinyl. Unless set forth or recited to the contrary, all heteroaryl groups described or claimed herein may be substituted or unsubstituted.

The term "arylalkyl" refers to an aryl group as defined above directly bonded to an alkyl group as defined above, e.g., —$CH_2C_6H_5$ and —$C_2H_4C_6H_5$. An arylalkyl group may, alternatively, be referred to as e.g. —($C_{1-6}$-alkyl)-aryl. Unless set forth or recited to the contrary, all arylalkyl groups described or claimed herein may be substituted or unsubstituted.

The term "heteroarylalkyl" refers to a heteroaryl ring radical directly bonded to an alkyl group. The heteroarylalkyl radical may be attached to the main structure at any carbon atom in the alkyl group that results in the creation of a stable structure. An heteroarylalkyl group may, alternatively, be referred to as e.g. —($C_{1-6}$-alkyl)-heteroaryl. Unless set forth or recited to the contrary, all heteroarylalkyl groups described or claimed herein may be substituted or unsubstituted.

With the groups of preferred compounds of formula (I) and N-oxides thereof mentioned hereinafter, definitions of substituents from the general definitions mentioned hereinbefore may reasonably be used, e.g. to replace more general definitions with more specific definitions or especially with definitions characterized as being preferred.

Any asymmetric carbon atom may be present in the (R)-, (S)- or (R,S)-configuration. The compounds may thus be present as mixtures of stereoisomers or as pure stereoisomers. The invention relates also to possible tautomers of the compounds of formula (I).

Where the plural form is used for compounds, salts and the like, this is taken to mean also a single compound, salt or the like.

Salts of compounds of formula (I) are the physiologically acceptable salts. Physiologically acceptable salts are particularly suitable for medical applications, due to their greater solubility in water compared with the starting or base compounds. Suitable physiologically acceptable acid addition salts of the compounds of the invention may be salts of inorganic acids such as hydrochloric acid, hydrobromic acid, phosphoric acid, and the like or of organic acids such as, for example, acetic acid, benzenesulfonic acid, methanesulfonic acid, benzoic acid, citric acid, glycolic acid, lactic acid, fumaric acid, succinic acid, adipic acid, pimelic acid, suberic acid, azelaic acid, malic acid, tartartic acid, amino acids, such as glutamic acid or aspartic acid, and the like. Examples of suitable physiologically acceptable basic salts are ammonium salts, or suitable organic amines, such as tertiary monoamines, e.g. triethylamine or tris(2-hydroxyethyl)amine etc., alkali metal salts such as sodium salts and potassium salts and alkaline earth metal salts such as magnesium salts and calcium salts. When a basic group and an acid group are present in the same molecule, a compound of formula (I) may also form internal salts.

For isolation or purification purposes it is also possible to use pharmaceutically unacceptable salts, e.g. picrates or perchlorates. For therapeutic use, only pharmaceutically acceptable salts or free compounds are employed and these are therefore preferred.

In view of the close relationship between the novel compounds in free form and those in the form of their salts, including those salts and that can be used as intermediates, e.g. in the purification or identification of the novel compounds, any reference to the free compounds hereinbefore and hereinafter is to be understood as referring also to the corresponding salts, as appropriate and expedient.

The embodiments below are illustrative of the present invention and are not intended to limit the claims to the specific embodiments exemplified. It is also to be understood that the embodiments defined herein may be used independently or in conjunction with any definition, claim or any other embodiment defined herein. Thus the invention contemplates all possible combinations and permutations of the various independently described embodiments.

In one embodiment, specifically provided are compounds of formula (I) in which ring P and ring Q are independently selected from an aryl ring having 6 to 14 carbon atoms, or a 5 to 14 membered heteroaryl ring containing one to four hetero atoms (e.g. one, two, three or four hetero atoms) each independently selected from O, S and N, optionally substituted by one or more identical or different radicals $R_3$, with a proviso that when ring Q is pyridyl then ring P is heteroaryl.

In an embodiment, P is selected from the group consisting of quinolinyl, pyridinyl, benzothiazolyl, imidazo[1,2-a]pyrazinyl, imidazo[1,2-a]pyridazinyl, pyrimidinyl, imidazo[1,2-a]pyridinyl, pyrazinyl, quinazolinyl, pyrazolo[1,5-a]pyrimidinyl, pyrido[2,3-b]pyrazinyl, imidazo[1,2-b]pyridazinyl, naphthyl and 2H-pyrazolyl.

In an embodiment, P is substituted with a single $R_3$ radical or two independently selected $R_3$ radicals. Preferably, P is substituted with a single $R_3$ radical. In an embodiment, when P is substituted with a single $R_3$ radical, the $R_3$ radical is selected from the group consisting of: halo (e.g. Cl or F) and $C_{1-6}$ alkyl (e.g., methyl, ethyl, n-propyl, 1-methylethyl (isopropyl), n-butyl, n-pentyl, and 1,1-dimethylethyl (t-butyl).). Preferably, when P is substituted with a single $R_3$ radical, the $R_3$ radical is selected from the group consisting of: Cl, F, Me and t-Bu. Preferably, when P is substituted with two independently selected $R_3$ radicals, the $R_3$ radical is selected from the group consisting of: $C_{1-6}$ alkyl (e.g., methyl, ethyl, n-propyl, 1-methylethyl (isopropyl), n-butyl, n-pentyl, 1,1-dimethylethyl (t-butyl) and aryl (e.g. phenyl).

In an embodiment, P is unsubstituted.

In an embodiment, P is selected from the group consisting of 3-quinolinyl, 3-pyridinyl, 6-quinolinyl, 2-benzothiazolyl, imidazo[1,2-a]pyrazinyl, imidazo[1,2-a]pyridazinyl, 3-pyrimidinyl, imidazo[1,2-a]pyridinyl, 2-pyrazinyl, 7-chloro-3-quinazolinyl, 3-quinazolinyl, pyrazolo[1,5-a]pyrimidinyl, pyrido[2,3-b]pyrazinyl, imidazo[1,2-b]pyridazinyl, 6-methyl-3-quinolinyl, 3-naphthyl, 5-t-butyl-2-phenyl-2H-pyrazolyl, 6-chloro-3-quinolinyl, 6-fluoro-3-quinolinyl and 2-quinolinyl.

According to another embodiment, specifically provided are compounds of the formula (I) wherein ring P is a 5 to 14 membered heteroaryl ring containing one to four hetero atoms each independently selected from O, S and N. Preferably the heteroaryl ring is selected from the group consisting of pyridine, thiophene, pyrazole, thiazole, quinoline, benzothiazole, pyrazine, pyrimidine, quinoxaline, quinazoline, imidazo[1,2-a]pyrazine, imidazo[1,2-a]pyridazine, imidazo[1,2-a]pyridine, pyrazolo[1,5-a]pyrimidine, pyrido[2,3-b]pyrazine, cinnoline, phthalazine, optionally substituted by one or more identical or different radicals $R_3$.

In yet another embodiment, the preferred compounds of formula (I) are selected from the compounds wherein the ring P is an optionally substituted naphthyl ring. The naphthyl ring is optionally substituted with one or more identical or different radicals $R_3$.

In yet another embodiment, specifically provided are compounds of the formula (I) wherein ring Q is a 5 to 14 membered heteroaryl ring containing one to four hetero atoms each independently selected from O, S and N. Preferably the heteroaryl ring is selected from the group consisting of pyridine, thiophene, pyrazole and thiazole, optionally substituted by one or more identical or different radicals $R_3$. In an embodiment in which Q is a 5 to 14 membered heteroaryl ring containing one to four hetero atoms each independently selected from O, S and N, the heteroaryl ring is unsubstituted.

In an embodiment, Q is substituted with a single $R_3$ radical. In an embodiment, Q is substituted with a two independently selected $R_3$ radicals. In an embodiment, Q is unsubstituted.

In an embodiment, the Q is a heteroaryl ring selected from the group consisting of:

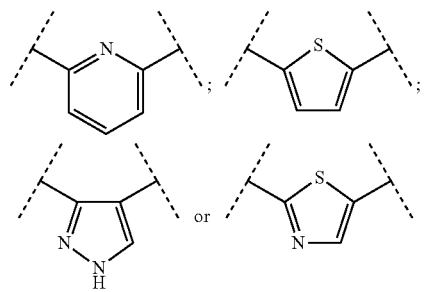

wherein the dashed lines indicate the point of attachment to the rest of the compound of formula (I) (i.e. the left hand dashed line is the point of attachment to the 1,2-acetylenic bond and the right hand dashed line is the point of attachment to X).

In yet another embodiment, the preferred compounds of formula (I) are selected from the compounds in which the ring Q is an optionally substituted phenyl ring, wherein the substituent is selected from —$C_{1-8}$-alkyl, —O—$C_{1-8}$-alkyl or halo group. Preferably, the —$C_{1-8}$-alkyl group is a methyl, the —O—$C_{1-8}$-alkyl is methoxy and the halo group is selected from fluorine (i.e. fluoro), chlorine (i.e. chloro) and bromine (i.e. bromo). Most preferably, the halo group is fluorine (i.e. fluoro). In an embodiment, Q is substituted with a single $R_3$ radical or is unsubstituted.

In an embodiment, Q is an aryl ring selected from the group consisting of phenyl;

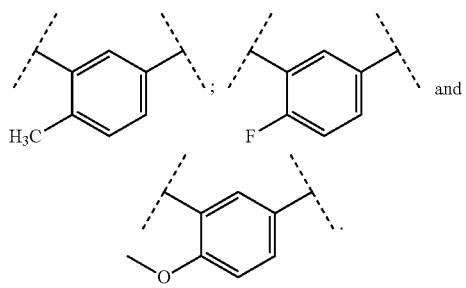

In another embodiment, the preferred compounds of formula (I) are selected from the compounds wherein X is selected from C=O and C=S. Preferably, X is C=O.

In another embodiment, the preferred compounds of formula (I) are selected from the compounds wherein X & Y may be same or different. Preferably, X & Y both are C=O.

In yet another embodiment, the preferred compounds of formula (I) are selected from the compounds wherein X is C=S. In yet another embodiment, the preferred compounds of formula (I) are selected from the compounds wherein X is C=S and Y is C=O.

In another embodiment, the compounds of formula (I) are selected from the compounds wherein $R_1$ is hydrogen.

In yet another embodiment, specifically provided are compounds of formula (I), wherein $R_1$ is selected from —$C_{1-8}$-alkyl, —$C_{2-10}$-alkenyl, —$C_{2-12}$-alkynyl, —$C_{3-12}$-cycloalkyl, —$C_{4-12}$-cycloalkylalkyl or a —$C_{3-12}$-cycloalkenyl group.

In another embodiment, the compounds of formula (I) are selected from the compounds wherein $R_1$ is selected from the group consisting of hydrogen and $C_{1-6}$ alkyl, preferably hydrogen and $C_{1-4}$ alkyl (e.g., methyl, ethyl, n-propyl, 1-methylethyl (isopropyl), n-butyl, n-pentyl, and 1,1-dimethylethyl (t-butyl). In an embodiment, $R_1$ is selected from the group consisting of hydrogen, methyl and t-butyl.

In another embodiment, the compounds of formula (I) are selected from the compounds wherein $R_2$ is selected from aryl, heteroaryl, arylalkyl or a heteroarylalkyl radical, wherein the aryl ring contains 6 to 14 carbon atoms, and the heteroaryl ring contains 5 to 14 membered ring system with one to four hetero atoms each independently selected from O, S and N, and are optionally substituted by one or more identical or different radicals $R_3$.

In yet another embodiment, specifically provided are compounds of formula (I), wherein $R_2$ is an aryl or a heteroaryl, ring selected from phenyl, pyridine, thiophene or pyrazole, optionally substituted by one or more identical or different radicals $R_3$.

In an embodiment when $R_2$ is an aryl or a heteroaryl ring selected from phenyl, pyridine, thiophene and pyrazole; the aryl or heteroaryl ring may be substituted with —$C_{1-6}$-alkyl (e.g., methyl, ethyl, n-propyl, 1-methylethyl (isopropyl), n-butyl, n-pentyl, and 1,1-dimethylethyl (t-butyl), halo (e.g. fluoro, chloro, bromo or iodo), —$C_{1-6}$-haloalkyl (e.g. —$C_{1-6}$-fluoroalkyl or —$C_{1-6}$-chloroalkyl), —O—$C_{1-6}$-alkyl (e.g. methoxy or ethoxy), —$N_3$, —$NO_2$, —($C_{1-8}$-alkyl)-heterocycloalkyl containing 3 to 12 rings atoms having one or two hetero atoms each independently selected from O, S and N, —($C_{1-4}$-alkyl)-heteroaryl group and aryl; wherein each of the aforementioned $R_3$ groups may be optionally substituted with a single group selected from the group consisting of $C_{1-4}$-alkyl (e.g. methyl or ethyl), $C_{1-4}$-alkoxy (e.g. methoxy or ethoxy), $C_{1-4}$-haloalkyl (e.g. $CF_3$), —OH, —COOH, —CN, —$NO_2$, halo (e.g. fluoro, chloro or bromo), —$NH_2$ and —$SO_2NH_2$.

In an embodiment when $R_2$ is an aryl or a heteroaryl ring selected from phenyl, pyridine, thiophene and pyrazole, the aryl or heteroaryl ring may be unsubstituted.

In an embodiment, when $R_2$ is an aryl or a heteroaryl ring selected from phenyl, pyridine, thiophene and pyrazole, the aryl or heteroaryl ring may be substituted with a single $R_3$ radical.

In an embodiment, when $R_2$ is an aryl or a heteroaryl ring selected from phenyl, pyridine, thiophene and pyrazole, the aryl or heteroaryl ring may be substituted with two independently selected $R_3$ radicals.

In an embodiment, when $R_2$ is an aryl or a heteroaryl ring selected from phenyl, pyridine, thiophene and pyrazole, the aryl or heteroaryl ring may be substituted with three independently selected $R_3$ radicals.

In an embodiment, the $R_2$ radical is an aryl or heteroaryl ring selected from the group consisting of

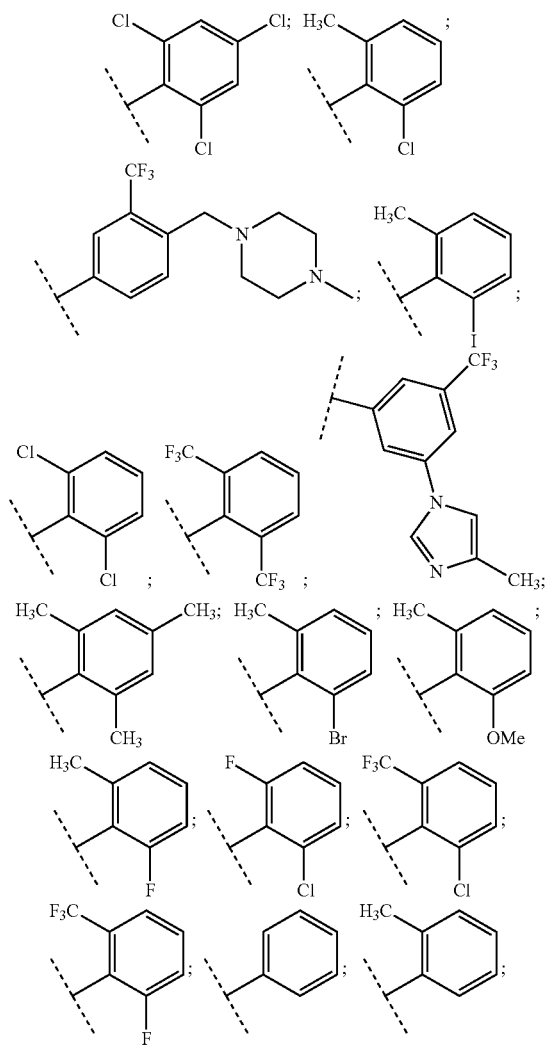

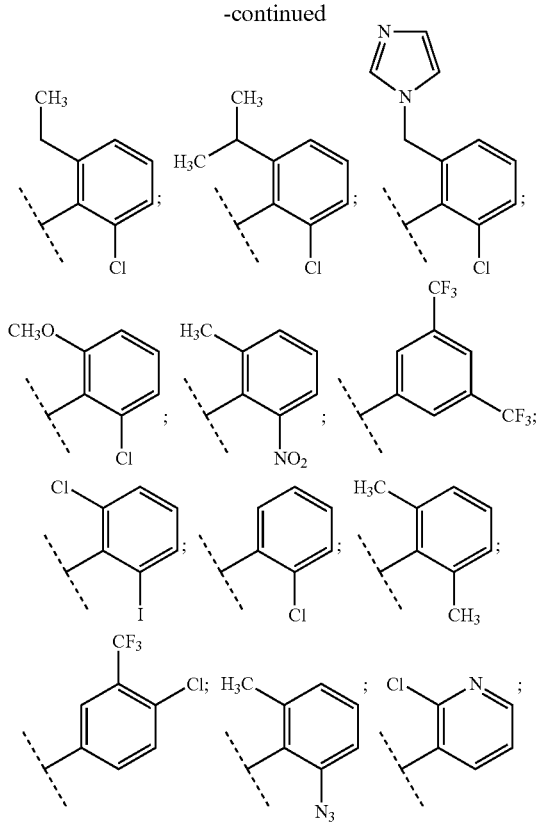

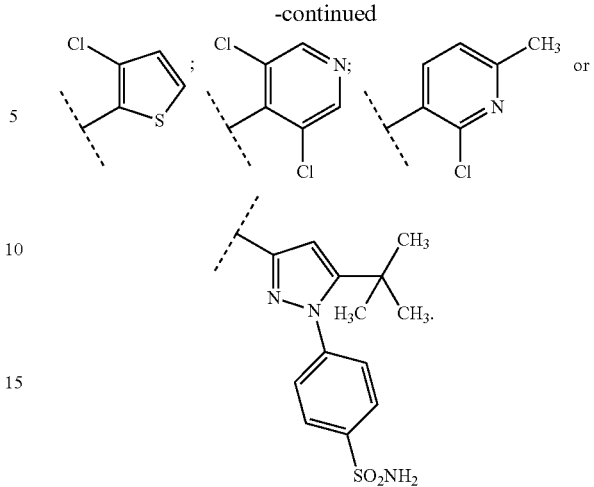

In another embodiment, specifically provided are compounds of formula (I) in which X & Y both are C=O, $R_1$ is hydrogen and $R_2$ is aryl or heteroaryl. In yet another embodiment, the present invention provides an N-oxide of compound of formula (I).

In yet another embodiment, the present invention provides a compound of formula (I) and a physiologically acceptable salt, thereof.

The compounds of the present invention can be exemplified by the following non-limiting examples:

| Compound No. | Chemical Name |
|---|---|
| I.1 | 2,4,6-Trichloro-N'-[4-methyl-3-[2-(3-quinolyl)ethynyl]benzoyl]-benzohydrazide |
| I.2 | N'-(2-Chloro-6-methylbenzoyl)-4-methyl-3-[2-(3-quinolyl)ethynyl]-benzohydrazide |
| I.3 | 4-Methyl-N'-[4-[(4-methylpiperazin-1-yl)methyl]-3-(trifluoromethyl) benzoyl]-3-[2-(3-quinolyl)ethynyl]benzohydrazide |
| I.4 | N'-(2-Iodo-6-methylbenzoyl)-4-methyl-3-[2-(3-quinolyl)ethynyl]-benzohydrazide |
| I.5 | N'-(2,6-Dichlorobenzoyl)-4-methyl-3-[2-(3-quinolyl)ethynyl]-benzohydrazide |
| I.6 | N'-[2,6-Bis(trifluoromethyl)benzoyl]-4-methyl-3-[2-(3-quinolyl)-ethynyl]benzohydrazide |
| I.7 | 4-Methyl-N'-[3-(4-methylimidazol-1-yl)-5-(trifluoromethyl)benzoyl]-3-[2-(3-quinolyl)ethynyl]benzohydrazide |
| I.8 | 2,4,6-Trimethyl-N'-[4-methyl-3-[2-(3-quinolyl)ethynyl]benzoyl]-benzohydrazide |
| I.9 | N'-(2-Chloro-6-methylbenzoyl)-4-methyl-3-[2-(3-pyridyl)ethynyl]-benzohydrazide |
| I.10 | N'-(2-Chloro-6-methylbenzoyl)-4-methyl-3-[2-(6-quinolyl)ethynyl]-benzohydrazide |
| I.11 | N'-(2-Bromo-6-methylbenzoyl)-4-methyl-3-[2-(3-quinolyl)ethynyl]-benzohydrazide |
| I.12 | 3-[2-(1,3-Benzothiazol-2-yl)ethynyl]-N'-(2-chloro-6-methylbenzoyl)-4-methylbenzohydrazide |
| I.13 | N'-(2-Methoxy-6-methylbenzoyl)-4-methyl-3-[2-(3-quinolyl)-ethynyl]benzohydrazide |
| I.14 | N'-(2-Fluoro-6-methylbenzoyl)-4-methyl-3-[2-(3-quinolyl)ethynyl]-benzohydrazide |
| I.15 | 2,4,6-Trichloro-N'-[3-[2-(2-imidazo[1,2-a]pyrazin-3-yl)ethynyl]-4-methylbenzoyl]benzohydrazide |
| I.16 | N'-(2-Chloro-6-methylbenzoyl)-3-[2-(imidazo[1,2-b]pyridazin-3-yl)-ethynyl]-4-methylbenzohydrazide |
| I.17 | N'-(2-Chloro-6-methylbenzoyl)-3-[2-(imidazo[1,2-a]pyrazin-3-yl)-ethynyl]-4-methylbenzohydrazide |
| I.19 | N'-(2-Chloro-6-methylbenzoyl)-3-[2-(imidazo[1,2-a]pyridin-3-yl)-ethynyl]-4-methylbenzohydrazide |
| I.20 | N'-(2-Chloro-6-methylbenzoyl)-4-methyl-3-[2-(pyrazin-2-yl)-ethynyl]benzohydrazide |

-continued

| Compound No. | Chemical Name |
|---|---|
| I.21 | N'-(2-Cchloro-6-methylbenzoyl)-4-fluoro-3-[2-(3-quinolyl)ethynyl]-benzohydrazide |
| I.22 | N'-(2-Chloro-6-methylbenzoyl)-4-methoxy-3-[2-(3-quinolyl)-ethynyl]benzohydrazide |
| I.23 | N'-(2-Fluoro-6-iodobenzoyl)-4-methyl-3-[2-(3-quinolyl)ethynyl]-benzohydrazide |
| I.24 | N'-[2-Chloro-6-(trifluoromethyl)benzoyl]-4-methyl-3-[2-(3-quinolyl)ethynyl]benzohydrazide |
| I.25 | N'-[2-Fluoro-6-(trifluoromethyl)benzoyl]-4-methyl-3-[2-(3-quinolyl)-ethynyl]benzohydrazide |
| I.26 | N'-(2-Chloro-6-methylbenzoyl)-3-[2-(7-chloroquinoxalin-2-yl)-ethynyl]-4-methylbenzohydrazide |
| I.27 | N'-(2-Chloro-6-methylbenzoyl)-4-methyl-3-[2-(quinoxalin-2-yl)-ethynyl]benzohydrazide |
| I.28 | N'-(Benzoyl)-4-methyl-3-[2-(3-quinolyl)ethynyl]benzohydrazide |
| I.29 | N'-(2-Chloronicotinyl)-4-methyl-3-[2-(3-quinolyl)ethynyl]benzohydrazide |
| I.30 | N'-(2-Methylbenzoyl)-4-methyl-3-[2-(3-quinolyl)ethynyl]benzo-hydrazide |
| I.31 | N'-(2-Chloro-6-ethylbenzoyl)-4-methyl-3-[2-(3-quinolyl)ethynyl]-benzohydrazide |
| I.32 | N'-(2-Chloro-6-isopropylbenzoyl)-4-methyl-3-[2-(3-quinolyl)-ethynyl]benzohydrazide |
| I.33 | N'-[2-Chloro-6-(imidazol-1-yl)methylbenzoyl[-4-methyl-3-[2-(3-quinolyl)ethynyl]benzohydrazide |
| I.34 | N'-(2-Chloro-6-methoxybenzoyl)-4-methyl-3-[2-(3-quinolyl)-ethynyl]benzohydrazide |
| I.35 | N'-(2-Chloro-6-methylbenzoyl)-4-methyl-3-[3-(pyrazolo(1,5-a)-pyrimidin-6-yl)ethynyl]benzohydrazide |
| I.36 | N'-(2-Methyl-6-nitrobenzoyl)-4-methyl-3-[2-(3-quinolyl)ethynyl]-benzohydrazide |
| I.37 | N'-[3,5-bis-trifluoromethylbenzoyl]-4-methyl-3-[2-(3-quinolyl)-ethynyl]benzohydrazide |
| I.38 | N'-(2-Chloro-6-methylbenzoyl)-4-methyl-3-[(pyrido(2,3-b)pyrazin-7-yl)ethynyl]benzohydrazide |
| I.39 | N'-(2-Chloro-6-iodobenzoyl)-4-methyl-3-[2-(3-quinolyl)ethynyl]-benzohydrazide |
| I.40 | N'-(2-Chlorobenzoyl)-4-methyl-3-[2-(3-quinolyl)ethynyl]benzo-hydrazide |
| I.41 | N'-(2,6-Dichlorobenzoyl)-4-methyl-3-[(imidazo(1,2-b)pyridazin-3-yl)ethynyl]benzohydrazide |
| I.42 | N'-(2-Chloro-6-methylbenzoyl)-4-methyl-3-[(imidazo(1,2-a)pyridin-3-yl)ethynyl]benzohydrazide |
| I.43 | N-tert-Butyl-N'-(2-chloro-6-methylbenzoyl)-4-methyl-3-[2-(3-quinolyl)ethynyl]benzohydrazide |
| I.44 | N'-(2-Chloro-6-methylbenzoyl)-4-methyl-3-[2-(6-methyl-3-quinolyl)ethynyl]benzohydrazide |
| I.45 | N-Methyl-N'-(2-Chloro-6-methylbenzoyl)-4-methyl-3-[2-(3-quinolyl)ethynyl]benzohydrazide |
| I.46 | N'-(2,6-Dimethylbenzoyl)-4-methyl-3-[2-(3-quinolyl)ethynyl]benzo-hydrazide |
| I.47 | N'-(4-Chloro-3-trifluoromethylbenzoyl)-4-methyl-3-[2-(3-quinolyl)-ethynyl]benzohydrazide |
| I.48 | N'-(2-Chloro-6-methylbenzoyl)-4-methyl-3-[2-naphthyl)ethynyl]-benzohydrazide |
| I.49 | N'-(2-Chloro-6-methylbenzoyl)-4-methyl-3-[2-(5-tert-butyl-2-phenyl-2H-pyrazol-3-yl)ethynyl]benzohydrazide |
| I.50 | N'-(2-Chloro-6-methylbenzoyl)-4-methyl-3-[2-(6-chloro-3-quinolyl)-ethynyl]benzohydrazide |
| I.51 | N'-(3-Chloro-2-thiophenyl)-4-methyl-3-[2-(3-quinolyl)ethynyl]-benzohydrazide |
| I.52 | N'-(2-Azido-6-methylbenzoyl)-4-methyl-3-[2-(3-quinolyl)ethynyl]-benzohydrazide |
| I.53 | N'-(3,5-Dichloroisonicotinoyl)-4-methyl-3-[2-(3-quinolyl)ethynyl]-benzohydrazide |
| I.54 | N'-(5-tert-Butyl-1-benzenesulfonyl-1-pyrazolyl)-4-methyl-3-[2-(3-quinolyl)ethynyl]benzohydrazide |
| I.55 | N'-(2-Chloro-6-methylbenzoyl)-4-methyl-3-[2-(6-fluoro-3-quinolyl)-ethynyl]benzohydrazide |
| I.56 | N'-(2-Chloro-6-methylbenzoyl)-4-methyl-3-[2-2-quinolyl)ethynyl]-benzohydrazide |
| I.57 | N'-(2-Chloro-6-fluorobenzoyl)-4-methyl-3-[2-(3-quinolyl)ethynyl]-benzohydrazide |
| I.58 | N'-(2-Chloro-6-methylnicotinoyl)-4-methyl-3-[2-(3-quinolyl)-ethynyl]benzohydrazide |
| I.59 | N'-(2-Chloro-6-methylbenzoyl)-3-[2-(3-quinolyl)ethynyl]benzo-hydrazide |

-continued

| Compound No. | Chemical Name |
|---|---|
| I.60 | N'-(2-Chloro-6-methylbenzoyl)-6-[2-(3-quinolyl)ethynyl]pyridine-2-carboxylic acid hydrazide |
| I.61 | N'-(2-Chloro-6-methylbenzoyl)-5-[2-(3-quinolyl)ethynyl]thiophene-2-carboxylic acid hydrazide |
| I.62 | N'-(2-Chloro-6-methylbenzoyl)-3-[2-(3-quinolyl)ethynyl]pyrazole-4-carboxylic acid hydrazide |
| I.63 | N'-(2-Chloro-6-methylbenzoyl)-2-[2-(3-quinolyl)ethynyl]thiazole-5-carboxylic acid hydrazide |
| I.64 | 2-Chloro-6-methyl-N'-[4-methyl-3-[2-(3-quinolyl)ethynyl]-thiobenzoyl]benzohydrazide |

The present invention provides a process for the preparation of compounds of formula (I) by condensation of the hydrazide of formula (III) with the diarylacetylenic compound of formula (II), wherein P, Q, X, Y, $R_1$ & $R_2$ are as previously defined for compound of formula (I), and L is a leaving group and is depicted below in Scheme 1.

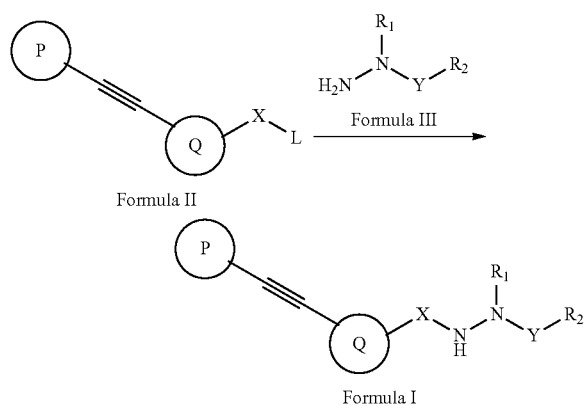

Scheme 1

Formula II

Formula III

Formula I

Preferably the condensation reaction is carried out in the presence of an inert base and/or a suitable catalyst in an inert solvent. The compound of formula (II), which is in activated form, can alternatively be generated in situ from the corresponding acid (i.e. when X═CO and L═OH) and then condensed with the compound of formula (III) to generate the compound of formula (I).

A derivative of the formula (II) in activated form (i.e. —X-L) is especially an acid halide, an ester, a reactive ester, a reactive anhydride or a reactive cyclic amide.

Formula (II) wherein X-L is an acid halide group, can be obtained, for example, by treatment of the corresponding acid (i.e. when X═CO and L═OH) with a halogenating agent such as thionyl chloride, phosphorus pentachloride or oxalyl chloride.

Reactive esters of formula (II) are especially for example vinyl esters obtainable, for example, by transesterification of a corresponding ester with vinyl acetate, carbamoylvinyl esters or by treatment with a $C_{2-5}$ alkoxyacetylene. Other active esters are of the amidino type, such as N,N'-disubstituted amidino esters (obtainable, for example, by treatment of the corresponding acid with a suitable N,N'-disubstituted carbodiimide, for example, N,N'-dicyclohexylcarbodiimide), or N,N'-disubstituted amidino esters (obtainable, for example, by treatment of the corresponding acid with N,N-disubstituted cyanamide), suitable aryl esters, especially phenyl esters suitably substituted by electron-attracting substituents (obtainable, for example, by treatment of the corresponding acid with a suitably substituted phenol, for example, 4-nitrophenol, 2,4,5-trichlorophenol, or 2,3,4,5,6-pentachloro-phenol in the presence of a condensation agent, such as N,N'-dicyclohexylcarbodiimide). Other suitable active esters include cyanomethyl esters (obtainable, for example, by treatment of the corresponding acid with chloroacetonitrile in the presence of a base), thio esters, especially unsubstituted or substituted, for example nitro-substituted, phenylthio esters (obtainable, for example, by treatment of the corresponding acid with unsubstituted or substituted, for example nitro-substituted, thiophenols, inter alia by the anhydride or carbodiimide method), amino or amido esters (obtainable, for example, by treatment of the corresponding acid with an N-hydroxyamino or N-hydroxyamido compound, for example, N-hydroxysuccinimide, N-hydroxypiperidine, N-hydroxyphthalimide or 1-hydroxybenzotriazole, for example by the anhydride or carbodiimide method).

Other activated forms of formula (II) may be as anhydrides. Anhydrides may be with carbonic acid semiderivatives, such as corresponding esters, for example carbonic acid alkyl semiesters (obtainable, for example, by treatment of the corresponding acid with haloformic, such as chloroformic, acid); alkyl esters or with a 1-alkoxycarbonyl-2-alkoxy-1,2-dihydroquinoline, for example 1-alkoxycarbonyl-2-ethoxy-1,2-dihydroquinoline; anhydrides with dihalogenated, especially dichlorinated phosphoric acid (obtainable, for example, by treatment of the corresponding acid with phosphorus oxychloride), or anhydrides with organic acids, such as mixed anhydrides with organic carboxylic acids (obtainable, for example, by treatment of the corresponding acid with an unsubstituted or substituted acyl halide, for example, pivaloyl chloride or trifluoroacetyl chloride). Anhydrides may also be with organic sulfonic acids (obtainable, for example, by treatment of a salt, such as an alkali metal salt, of the corresponding acid, with a suitable organic sulfonic acid halide, such as alkane- or aryl-, for example methane- or p-toluenesulfonyl chloride), or with organic phosphonic acids (obtainable, for example, by treatment of the corresponding acid with a suitable organic phosphonic anhydride or phosphonic cyanide).

Suitable cyclic amides are especially amides with five-membered diazacycles of aromatic character, such as with imidazoles (obtainable, for example, by treatment of the corresponding acid with N,N'-carbonyldiimidazole; imidazolide method), or pyrazoles, for example 3,5-dimethylpyrazole.

Formula (II) in activated form is preferably generated in situ from the corresponding acid (i.e. when X═CO and L═OH). For example, N,N'-disubstituted amidino esters can be formed in situ by reacting a mixture of the acid of formula (II) (i.e. when X═CO and L═OH) and the compound of formula (III) in the presence of a suitable condensating agent for example N,N'-dicyclohexylcarbodiimide. Reactive mixed anhydrides of the acid may also be generated with an organic phosphonic acid in situ by reaction with propylphosphonic anhydride or diethylcyanophosphonate in the presence of suitable base for e.g. triethylamine or 4-(N,N-dimethylamino)pyridine.

The reaction may be carried out in a manner known per se, the reaction conditions being dependent especially on how the acid group of formula (II) has been activated, usually in the presence of a suitable solvent or diluent or of a mixture thereof and, if necessary, in the presence of a condensation agent. Customary condensation agents are, for example, carbodiimides such as N,N'-diethyl-, N,N'-diisopropyl, N,N'-dicyclohexyl- or N-ethyl-N'-(3-diethylaminopropyl)-carbodiimide; suitable carbonyl compounds, for example carbonyldiimidazole, or 1,2-oxazolium compounds, for example 2-ethyl-5-phenyl-1,2-oxazolium 3'-sulfonate and 2-tert-butyl-5-methyl-isoxazolium perchlorate, or a suitable acylamino compound, for example, 2-ethoxy-1-ethoxycarbonyl-1,2-dihydroquinoline. The bases normally used for aiding the condensation are either inorganic bases such as sodium or potassium carbonate, or organic bases, such as pyridine, triethyamine, N,N-diisopropylethylamine or 4-(dimethylamino)pyridine.

Alternatively, the preparation of compounds of formula (I) in the present invention can be performed by reacting compounds of formula (IV) with the compounds of formula (V), Scheme 2, using similar condensation methods as described above (for Scheme 1); wherein P, Q, X, Y, $R_1$ & $R_2$ and L are as previously defined.

Scheme 2

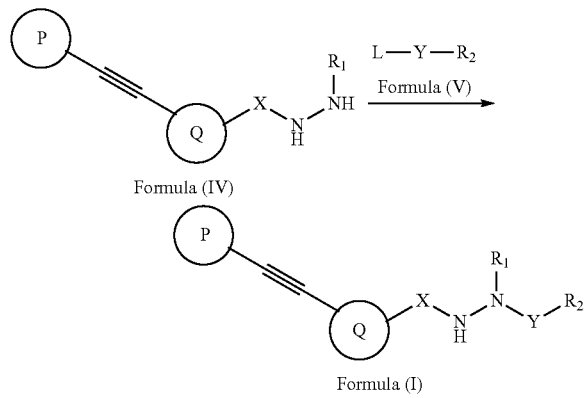

Formula (IV)

Formula (I)

Compounds of formula (IV) can be prepared from compounds of formula (II) and hydrazine of formula (IIIa), Scheme 3, utilizing the coupling procedures as described for Scheme 1, vide supra.

Scheme 3

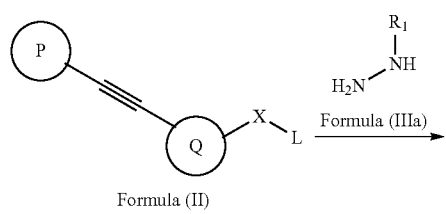

Formula (II)

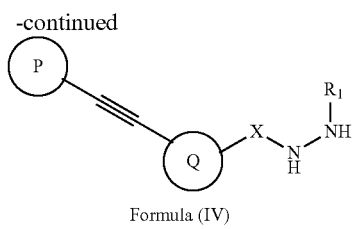

Formula (IV)

In a similar manner the compounds of formula (III) can be prepared by the reaction of compounds of formula (IIIa) and formula (V), Scheme 4.

Scheme 4

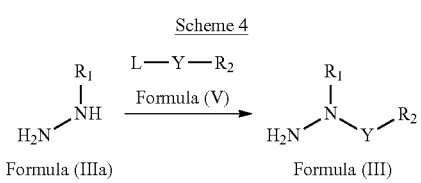

Formula (IIIa)    Formula (III)

Where the above starting compounds (II), (IIIa) and (IV) contain functional groups that may interfere with the coupling reaction, they are preferably protected using suitable protecting groups like trialkylsilyl, urethane groups such as tert-butyloxycarbonyl, benzyloxycarbonyl, tetrahydropyranyl, benzyl esters etc. that can be conveniently removed later.

The compounds of formula (II) can be prepared by methods known in the literature. Suitable approaches for the preparation of the compounds for formula (II) are provided in Scheme 5.

Scheme 5

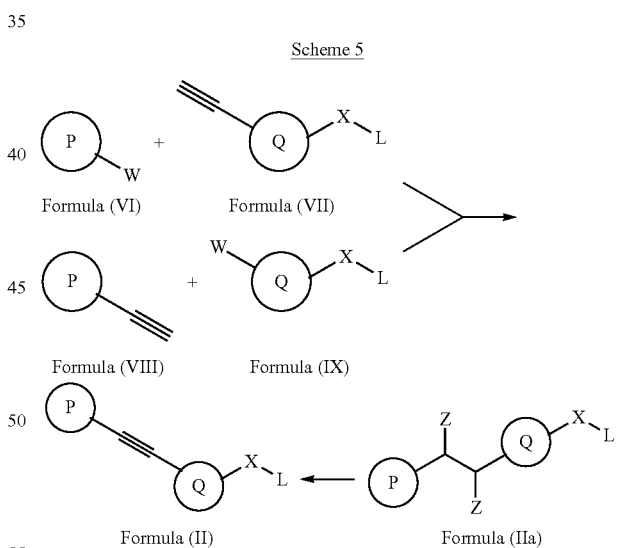

Formula (VI)    Formula (VII)

Formula (VIII)    Formula (IX)

Formula (II)    Formula (IIa)

As illustrated in Scheme 5, the ethynyl moiety of ring P of formula (VIII) is coupled with ring Q of formula IX, or the ethynyl moiety of ring Q of formula (VII) is coupled with ring P of formula VI; wherein 'W' represents OTf, Cl, Br or I, preferably Br or I; X as defined above and L represent OH or O-alkyl. The coupling reaction can be performed using well known prior art methods, such as metal catalyzed coupling reactions, for example a palladium catalyzed Sonogashira coupling reaction (refer Malleron, J.-L., Fiaud, J.-C., Legros, J.-Y. Handbook of Palladium Catalyzed Organic Reactions, San Diego: Academic Press, 1997). Alternatively, the compound of formula (II) is prepared from the vicinal dihalo compound of formula (IIa) (where Z represents halo) by tandem dehydrohalogenations.

A strategy similar to the above can be utilized for the synthesis of compounds of formula (I) as shown in Scheme 6, i.e. coupling the ethynyl moiety of ring P of formula (VIII) to the Q ring in formula (XI), or the ethynyl moiety of ring Q of formula (X) to the P ring in formula (VI); wherein P, Q, W, X, Y, $R_1$ & $R_2$ are as previously defined.

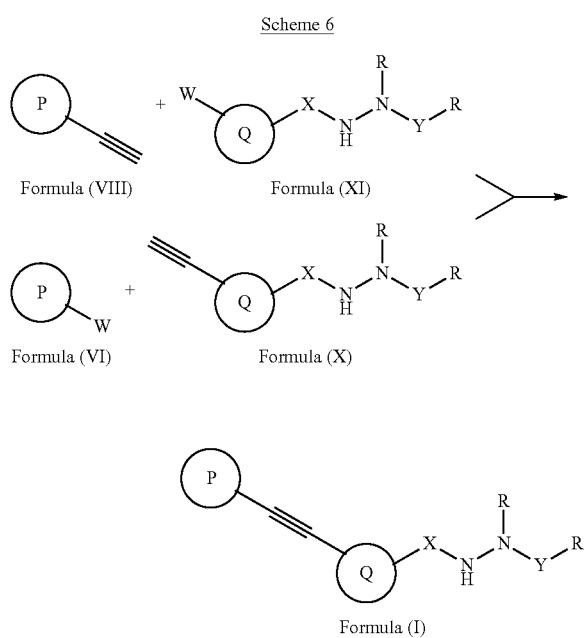

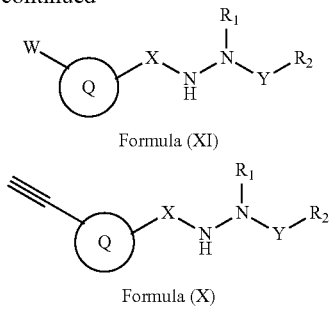

The compounds of formula (X) & formula (XI) can be conveniently prepared by acylation of the hydrazide of formula (III) with compounds of formula (VII) & formula (IX), respectively, as shown in Scheme 7; wherein L, Q, W, X, Y, $R_1$ & $R_2$ are as previously defined.

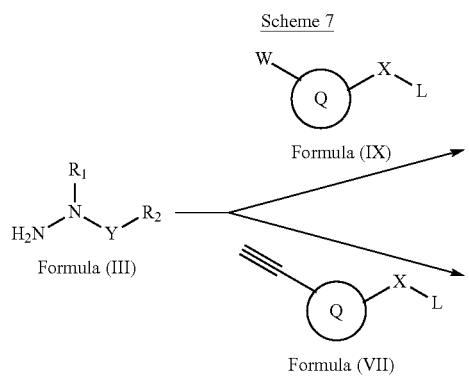

Where the above starting compounds (VI), (VII), (VIII) and (IX) contain functional groups that may interfere with the coupling reaction, are protected using suitable protecting groups that can be conveniently removed later.

With the synthetic approaches described vide supra, combined with the examples which follow and the additional information provided herein, the practitioner can prepare the full range of compounds disclosed herein.

If so desired, an obtainable compound of formula (I) is converted into another compound of formula I or an N-oxide thereof, a free compound of formula (I) is converted into a salt, an obtainable salt of a compound of formula (I) is converted into the free compound or another salt, and/or a mixture of isomeric compounds of formula (I) is separated into the individual isomers.

Salts of a compound of formula (I) with a salt forming group may be prepared in a manner known to those skilled in the art. Acid addition salts of compounds of formula (I) may thus be obtained by treatment with an acid, salt exchange, or with a suitable anion exchange reagent.

Stereoisomeric mixtures can be separated into their corresponding individual stereoisomers by means of suitable well known separation methods. Diastereomeric mixtures for example may be separated into their individual diastereomers by means of fractionated crystallization, chromatography, solvent distribution and other known procedures. This separation may be conducted either in a compound of formula (I) itself or at the level of a precursor compound. Enantiomers may be resolved by well known techniques for example through the formation of diastereomeric salts with enantiomer-pure chiral acid or a base; by derivatization with a suitable chiral derivatizing agent and separation such as by fractional crystallization, fractional distillation or by kinetic resolution such as enzymatic or chemical hydrolysis of the derivatized. Alternatively, the enantiomers may be resolved by means of chromatography, for example by chiral HPLC, using a chiral chromatographic stationary phase.

It should be emphasized that reactions analogous to the conversions mentioned herein may also take place at the level of appropriate intermediates.

Salts may be present in all starting compounds and transients, if these contain salt-forming groups. Salts may also be present during the reaction of such compounds, provided the reaction is not thereby disturbed.

At all reaction stages, isomeric mixtures that occur can be separated into their individual isomers, e.g. diastereomers or enantiomers, or into any mixtures of isomers, e.g. racemates or diastereomeric mixtures.

In the preferred embodiment, a compound of formula (I) is prepared according to or in analogy to the processes and process steps defined in the Examples.

The compounds of formula (I), including their salts, are also obtainable in the form of hydrates or solvates.

The compounds of formula (I) including their salts and N-oxides thereof, wherever applicable, have valuable pharmacological properties, as described hereinbefore and hereinafter.

In one embodiment, the present invention provides a method for treatment of disorders dependent on tyrosine kinases comprising administering to a mammal in need of such treatment an effective amount of compound of formula (I) or salt thereof.

A compound of formula (I) including their salts or an N-oxide thereof inhibits to varying degrees the receptor and non-receptor tyrosine kinases all of which play a role in growth regulation and transformation in mammalian cells, including human cells. The receptor tyrosine kinase may be kinases of the EGF family, e.g. ErbB2 kinase (HER-2), ErbB3 kinase, ErbB4 kinase; insulin-like growth factor receptor kinase (IGF-1 kinase), especially members of the PDGF-receptor tyrosine kinase family, such as PDGF-α & PDGF-β receptor kinase, JAK-2, CSF-1-receptor kinase, Phosphatidylinositol 3-kinases (PI 3-kinases or PI3Ks), AKT, CDK, mTOR, Kit-receptor kinase, Flt-3, Flt-4, FGFR-1, FGFR-3, FGFR-4, c-Met, RON, c-Ret, ALK and VEGF-receptor kinase. The non-receptor tyrosine kinase may be kinases such as Abl/Bcr-Abl kinase, Arg, kinases from the Src family, c-Src kinase, c-Yes, Lck, Lyn and Fyn.

The compounds of the present invention have been found to inhibit especially the Abl/Bcr-Abl kinase, including their mutant forms; Lyn and Lck kinases.

A compound of formula (I) including their salts or an N-oxide thereof inhibits to varying degrees the mutant forms of Abl/Bcr-Abl kinase which include the mutants of the P-loop of the kinase i.e. L248V, G250E, Q252H, Y253F & E255K; the C-helix mutants of the kinase i.e. D276G & E279K; the ATP binding region mutants of the kinase i.e. V299L, T315I & F317L; SH2-contact mutant of the kinase i.e. M351T; substrate binding region mutant of the kinase i.e. F359V; the A-loop mutants of the kinase i.e. L384M, H396P, H396R & G398R; and the C-terminal lobe mutant of the kinase i.e. F486S.

The compounds of the present invention have been found to inhibit especially the important mutants of the Abl/Bcr-Abl kinase viz. Q252H, Y253F, M351T, H396P, and more particularly the compounds of formula (I) inhibit the highly resistant form of the mutated kinase i.e. the T315I mutant.

The compounds of the present invention can be used to treat disorders dependent on tyrosine kinases especially chronic myelogenous leukemia (CML), chronic lymphocytic leukemia (CLL), acute lymphoblastic leukemia (ALL), acute myeloid leukemia (AML), myelodysplastic syndrome, melanoma, germ cell tumors, gastrointestinal stromal tumor (GIST), non-small cell lung carcinoma (NSCLC), mastocytosis, neuroblastoma, glioblastoma, astrocytoma, hepatocellular carcinoma, renal cell cancer, breast cancer, cutaneous systemic sclerosis, prostate and colorectal cancer and other solid tumors, diabetes remission.

On the basis of these studies, a compound of formula (I) according to the invention shows therapeutic efficacy especially against disorders dependent on TK, especially in proliferative diseases.

The present invention relates furthermore to a method for the treatment of a neoplastic disease which responds to an inhibition of a protein kinase activity, which comprises administering a compound of formula (I) or a N-oxide or a pharmaceutically acceptable salt thereof, wherein the radicals and symbols have the meanings as defined above for formula (I), in a quantity effective against said disease, to a warm-blooded animal requiring such treatment.

In particular the invention relates to a method for the treatment of proliferative disorders especially leukemia, irrespective of etiology of the disorder, which respond to inhibition of the aforementioned tyrosine kinases, particularly the Abl/Bcr-Abl tyrosine kinase and one or more of its several mutated forms. The treatment comprises administering a compound of formula (I) or an N-oxide or a pharmaceutically acceptable salt thereof, wherein the radicals and symbols have the meanings as defined above for formula (I), in a quantity effective against the particular disorder, to a warm-blooded animal requiring such treatment.

A compound of formula (I) can be administered alone or in combination with one or more other therapeutic agents, possible combination therapy taking the form of fixed combinations or the administration of a compound of the invention and one or more other therapeutic agents being staggered or given independently of one another, or the combined administration of fixed combinations and one or more other therapeutic agents. A compound of formula (I) can, besides or in addition, be administered especially for cancer therapy, such as leukemia or tumor therapy, in combination with chemotherapy, radiotherapy, immunotherapy, surgical intervention or a combination of these. Long-term therapy is equally possible as is adjuvant therapy in the context of other treatment strategies, as described above. Other possible treatments are therapy to maintain the patient's status after tumor regression, or even chemopreventive therapy, e.g. in patients at risk.

Therapeutic agents for possible combination include but are not limited to one or more non-receptor tyrosine kinase inhibitors such as imatinib, nilotinib, dasatinib and receptor tyrosine kinase inhibitors such as sorafenib, lapatinib, sunitinib, gefitinib, erlotinib, sirolimus, everolimus, temsirolimus; one or more other cytostatic or cytotoxic compounds, e.g. a chemotherapeutic agent or several selected from the group comprising antimetabolites such as antifolates (methotrexate, pemetrexed etc.), purine antagonists (6-mercaptopurine, fludarabine etc.) or pyrimidine antagonist (5-fluorouracil, capecitabine, gemcitabine etc.); indarubicin, hydroxyurea, busulfan, DNA alkylating/intercalating agent, an inhibitor of polyamine biosynthesis, inhibitor of microtubule depolymerization, topoisomerase I & II inhibitor, proteosome inhibitor, an inhibitor of protein kinase, especially of serine/threonine protein kinase, such as protein kinase C, an aromatase inhibitor. Other biological drugs for possible combination but not limited to include interferons (IFN-β), TGF-β; soluble receptor or other receptor antagonists implicated in cancer such as herceptin, avastin etc.

A compound according to the invention is not only for the (prophylactic and preferably therapeutic) management of humans, but also for the treatment of other warm-blooded animals, e.g. of commercially useful animals, e.g. rodents, such as mice, rabbits or rats, or guinea pigs. Such a compound may also be used as a reference standard in the test systems described above to permit a comparison with other compounds.

In general, the invention relates also to the use of a compound of formula (I) or an N-oxide thereof for the inhibition of tyrosine kinase activity, either in vitro or in vivo.

The present invention relates also to pharmaceutical compositions that comprise a compound of formula (I) or an N-oxide thereof as active ingredient and that can be used especially in the treatment of diseases mentioned at the beginning. Compositions for external administration, such as nasal, buccal, rectal or especially oral administration, and for parenteral administration, such as intravenous, intramuscular or subcutaneous administration, to warm-blooded animals, especially humans, are especially preferred. The compositions comprise the active ingredient alone or preferably together with a pharmaceutically acceptable carrier. The dosage of the active ingredient depends upon the disease to be treated and upon the species, its age, weight and individual condition, the individual pharmacokinetic data and the mode of administration.

The present invention relates especially to pharmaceutical compositions that comprise a compound of formula (I), a tautomer, an N-oxide or a pharmaceutically acceptable salt, or a hydrate or solvate thereof, and at least one pharmaceutically acceptable carrier.

The invention relates also to pharmaceutical compositions for use in a method for the prophylactic or especially therapeutic management of the human or animal body, to a process for the preparation thereof (especially in the form of compositions for the treatment of tumors) and to a method of treating diseases, especially those mentioned hereinabove.

The invention relates also to processes and to the use of compounds of formula (I) or N-oxides thereof for the preparation of pharmaceutical preparations which comprise compounds of formula (I) or N-oxides thereof as active component (active ingredient).

In the preferred embodiment, a pharmaceutical preparation is suitable for administration to warm-blooded animals, especially humans or commercially useful mammals suffering from disease responsive to inhibition of tyrosine kinase(s), for example inhibition of the Bcr-Abl tyrosine kinase for chronic myelogenous leukemia (CML), and comprises an effective quantity of a compound of formula (I) or N-oxides thereof for the inhibition of the Bcr-Abl fusion protein, or a pharmaceutically acceptable salt thereof, if salt-forming groups are present, together with at least one pharmaceutically acceptable carrier.

A pharmaceutical composition for the prophylactic or especially therapeutic management of neoplastic and other proliferative diseases of a warm-blooded animal, especially a human or a commercially useful mammal requiring such treatment, especially suffering from such a disease, comprising as active ingredient in a quantity that is prophylactically or therapeutically active against the said diseases a novel compound of formula (I) or N-oxides thereof, is likewise preferred.

The pharmaceutical compositions comprise from approximately 1% to approximately 95% active ingredient, single-dose administration forms comprising in the preferred embodiment from approximately 20% to approximately 90% active ingredient and forms that are not of single-dose type comprising in the preferred embodiment from approximately 5% to approximately 20% active ingredient. Unit dose forms are, for example, coated and uncoated tablets, ampoules, vials, suppositories or capsules. Further dosage forms are, for example, ointments, creams, pastes, foams, tinctures, sprays, etc. Examples are capsules containing from about 0.005 g to about 1.0 g active ingredient.

The pharmaceutical compositions of the present invention are prepared in a manner known per se, for example by means of conventional mixing, granulating, coating, dissolving or lyophilization processes.

Preference is given to the use of solutions of the active ingredient, and also suspensions or dispersions, especially isotonic aqueous solutions, dispersions or suspensions which, for example in the case of lyophilized compositions comprising the active ingredient alone or together with a carrier can be made up before use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilization processes. The said solutions or suspensions may comprise viscosity-increasing agents or solubilizers.

Pharmaceutical compositions for oral administration can be obtained, for example, by combining the active ingredient with one or more solid carriers, if desired granulating a resulting mixture, and processing the mixture or granules, if desired or necessary, by the inclusion of additional excipients, to form tablets or tablet cores.

Suitable carriers are especially fillers, such as sugars, cellulose preparations, and/or calcium phosphates, also binders such as starches, and/or poly(vinylpyrrolidone), and/or, if desired, disintegrators. Additional excipients are especially flow conditioners and lubricants.

Tablet cores can be provided with suitable, optionally enteric coatings, through the use of, inter alia, concentrated sugar solutions which may comprise gum arabic, talc, poly (vinylpyrrolidone), poly(ethylene glycol) and/or titanium dioxide, or coating solutions in suitable organic solvents or solvent mixtures, or, for the preparation of enteric coatings, solutions of suitable cellulose preparations.

Pharmaceutical compositions for oral administration also include hard capsules consisting of gelatin, also soft sealed capsules consisting of gelatin and a plasticizer. The hard capsules may contain the active ingredient in the form of granules, for example in admixture with fillers, binders, and/or glidants, and optionally stabilizers. In soft capsules, the active ingredient is preferably dissolved or suspended in suitable liquid excipients, to which stabilizers and detergents may also be added.

Pharmaceutical compositions suitable for rectal administration are, for example, suppositories that consist of a combination of the active ingredient and a suppository base.

For parenteral administration, aqueous solutions of an active ingredient in water-soluble form, for example of a water-soluble salt, or aqueous injection suspensions that contain viscosity-increasing substances, for example sodium carboxymethylcellulose, sorbitol and/or dextran, and if desired, stabilizers, are especially suitable. The active ingredient, optionally together with excipients, can also be in the form of a lyophilizate and can be made into a solution before parenteral administration by the addition of suitable solvents. Solutions that are used, for example, for parenteral administration can also be employed as infusion solutions.

The invention relates likewise to a process or a method for the treatment of one of the pathological conditions mentioned hereinabove, especially a disease which responds to an inhibition of a tyrosine kinase, especially a corresponding neoplastic disease. The compounds of formula (I) or N-oxides thereof can be administrated as such or especially in the form of pharmaceutical compositions, prophylactically or therapeutically, preferably in an amount effective against the said disease, to a warm-blooded animal, for example a human, requiring such treatment. In the case of an individual having a bodyweight of about 70 kg the daily dose administrated may be from approximately 0.005 g to approximately 5 g, preferably from approximately 0.05 g to approximately 1.0 g, of a compound of formula (I).

The present invention relates especially also to the use of a compound of formula (I) or N-oxides thereof, or a pharmaceutically acceptable salt thereof, as such or in the form of a pharmaceutical formulation with at least one pharmaceutically acceptable carrier for the therapeutic and also prophylactic management of one or more of the diseases mentioned hereinabove, preferably a disease which responds to an inhibition of a tyrosine kinase, especially a neoplastic disease.

The preferred dose, composition and preparation of pharmaceutical dosage forms which are to be used in each case are described above.

Experimental

The following examples serve to illustrate the invention without limiting the invention in its scope. The methods of preparing some of the starting compounds used in the examples are described as reference examples.

General Method of Preparation

The compounds described herein, including compounds of general formula (I), can be prepared by techniques known to in the art, for example, through the reaction scheme depicted in Schemes 1-7. Furthermore, in the following examples, where specific acids, bases, reagents, coupling agents, solvents, etc. are mentioned, it is understood that other suitable acids, bases, reagents, coupling agents etc. may be used and are included within the scope of the present invention. Modifications to reaction conditions, for example, temperature, duration of the reaction or combinations thereof are envisioned as part of the present invention. The compounds obtained by using the general reaction scheme may be of insufficient purity. These compounds can be purified by any of the methods for purification of organic compounds known in the art, for example, crystallization or silica gel or alumina column chromatography using different solvents in suitable ratios.

The following abbreviations are used in the text:
DMSO—dimethyl sulfoxide; DMF—N,N-dimethylformamide; THF-tetrahydrofuran; Pd(PPh$_3$)$_4$—tetrakis(triphenylphosphine)palladium; CuI—copper(I) iodide.

EXAMPLES

Reference Example 1

Methyl 3-ethynyl-4-methylbenzoate

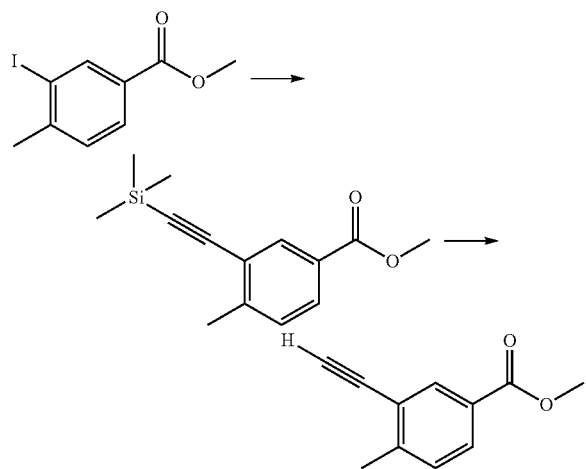

A mixture of methyl 3-iodo-4-methylbenzoate (2.0 g, 7 mmol), trimethylsilylacetylene (1.2 ml, 8 mmol), Pd(PPh$_3$)$_4$ (0.42 g, 0.3 mmol), CuI (0.137 g, 0.7 mmol) and diisopropylethylamine (2.5 ml, 11.4 mmol) in THF (20 ml) was heated at 50° C. for 12 hrs under nitrogen atmosphere. The reaction mixture was cooled to ambient temperature and filtered through a Celite® bed. The clear filtrate was concentrated and the residue purified by flash chromatography on silica gel (elution with 2% ethyl acetate in n-hexane) to provide methyl 4-methyl-3-[(trimethylsilyl)ethynyl]benzoate.

To the solution of methyl 4-methyl-3-[(trimethylsilyl) ethynyl]benzoate (2.3 g) in THF (40 ml) was added tetrabutylammonium fluoride (1.0M in THF, 3.2 ml, 11 mmol) at ambient temperature and stirred for 15 minutes, concentrated and the residue purified by flash chromatography on silica gel (elution with 2% ethyl acetate in n-hexane) to provide methyl 3-ethynyl-4-methylbenzoate.

$^1$H NMR (500 MHz in DMSO-d$_6$), δ2.50 (s, 3H), 3.90 (s, 3H), 4.57 (s, 1H), 7.51 (d, J=8.0 Hz, 1H), 7.91 (d, J=8.0 Hz, 1H), 7.99 (s, 1H).

Similarly were prepared the following ester compounds from their corresponding iodo esters:
Methyl 3-ethynyl-4-fluorobenzoate
Methyl 3-ethynyl-4-methoxybenzoate Reference Example 2

4-Methyl-3-[(quinolin-3-yl)ethynyl]benzoic acid

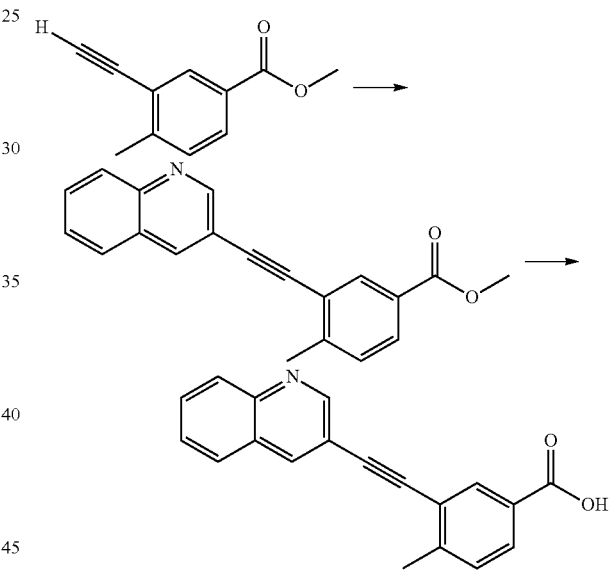

A mixture of methyl 3-ethynyl-4-methylbenzoate (0.341 g, 2 mmol), 3-iodoquinoline (0.5 g, 2 mmol), Pd(PPh$_3$)$_4$ (0.11 g, 0.01 mmol), CuI (0.179 g, 0.1 mmol) and diisopropylethylamine (0.5 ml, 3 mmol) in DMF (15 ml) was stirred at ambient temperature for 12 hrs under an atmosphere of nitrogen. The reaction mixture was concentrated and the crude product was purified by flash chromatography on silica gel (elution with 10% ethyl acetate in n-hexane) to provide methyl 4-methyl-3-[(quinolin-3-yl)ethynyl]benzoate.

Sodium hydroxide (0.15 g, 3.71 mmol) was added to a solution of the above methyl ester in methanol (20 ml) and water (3 ml) and stirred at 50° C. for 3 hrs and then concentrated in vacuo. Water (10 ml) was added to the residue, adjusted pH to 4.0-4.5 with citric acid. The solid obtained was filtered, washed successively with water and diethyl ether and dried at ambient temperature to obtain 4-methyl-3-[(quinolin-3-yl)ethynyl]benzoic acid.

$^1$H NMR (500 MHz in DMSO-d$_6$), δ 2.66 (s, 3H), 7.56 (d, J=8.0 Hz, 1H), 7.75 (t, J$_1$=15.1 Hz, J$_2$=8.2 Hz, 1H), 7.89 (t, J$_1$=13.7 Hz, J$_2$=8.5 Hz, 1H), 7.95 (d, J=8.0 Hz, 1H), 8.09 (d,

J=8.2 Hz, 1H), 8.12 (d, J=8.1 Hz, 1H), 8.17 (s, 1H), 8.75 (s, 1H), 9.11 (s, 1H), 12.84 (s, 1H).

Similarly were prepared the following acid compounds from the corresponding esters:
4-Methyl-3-[(pyridin-3-yl)ethynyl]benzoic acid
4-Methyl-3-[(quinolin-3-yl)ethynyl]benzoic acid
4-Methyl-3-[(benzothiazol-3-yl)ethynyl]benzoic acid
4-Fluoro-3-[(quinolin-3-yl)ethynyl]benzoic acid
4-Methoxy-[(3-quinolin-3-yl)ethynyl]benzoic acid
4-Methyl-3-[(pyrido(2,3-b)pyrazin-7-yl)ethynyl]benzoic acid
4-Methyl-3-[(6-methyl-3-quinolin-3-yl)ethynyl]benzoic acid
4-Methyl-3-[(naphth-3-yl)ethynyl]benzoic acid
4-Methyl-3-[5-tert-butyl-2-phenyl-2H-pyrazol-3-ylethynyl]benzoic acid
4-Methyl-3-[(6-chloro-3-quinolin-3-yl)ethynyl]benzoic acid
4-Methyl-3-[(6-fluoro-3-quinolin-3-yl)ethynyl]benzoic acid
4-Methyl-3-[(2-quinolin-3-yl)ethynyl]benzoic acid Reference Example 3

4-Methyl-3-[2-(3-quinolyl)ethynyl]benzohydrazide

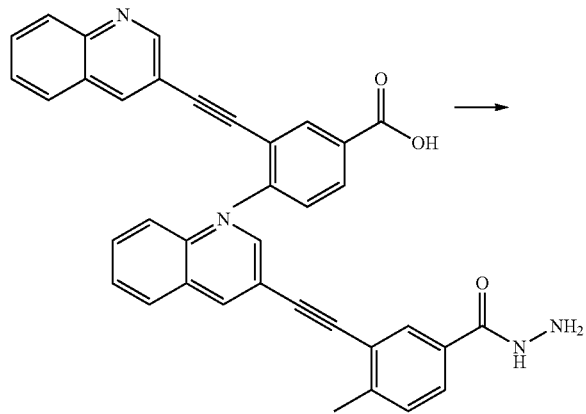

A mixture of 4-methyl-3-[(quinolin-3-yl)ethynyl]benzoic acid (0.15 g, 0.5 mmol), N-(3-dimethylaminopropyl)-N'-ethylcarbodiimide hydrochloride (0.15 g, 0.7 mmol) and 1-hydroxybenzotriazole (0.1 g, 0.7 mmol) in N,N-dimethylformamide (15 ml) was stirred at room temperature for 1 hr. Hydrazine hydrate (1.52 ml, 0.5 mmol) was then added and the mixture stirred for another 3 hrs. Concentration and trituration of the residue with water produced a solid which was filtered, washed successively with water and diethyl ether, and finally dried in vacuo to get the hydrazide as a pale yellow solid.

$^1$H NMR (400 MHz in DMSO-$d_6$), δ 2.63 (s, 3H), 4.79 (s, 2H), 7.51 (d, J=8.0 Hz, 1H), 7.75 (t, $J_1$=14.7 Hz, $J_2$=7.6 Hz, 1H), 7.85-7.96 (m, 2H), 8.09-8.13 (m, 3H), 8.73 (s, 1H), 9.09 (s, 1H), 9.91 (s, 1H).

Similarly were prepared the following acid hydrazide compounds from the corresponding acids:
4-Methyl-3-[2-(3-pyridyl)ethynyl]benzohydrazide
4-Methyl-3-[2-(6-quinolyl)ethynyl]benzohydrazide
3-[2-(1,3-Benzothiazol-2-yl)ethynyl]-4-methylbenzohydrazide
4-Fluoro-3-[2-(3-quinolyl)ethynyl]benzohydrazide
4-Methoxy-3-[2-(3-quinolyl)ethynyl]benzohydrazide
4-Methyl-3-[(pyrido(2,3-b)pyrazin-7-yl)ethynyl]benzohydrazide
4-Methyl-3-[(6-methyl-3-quinolin-3-yl)ethynyl]benzohydrazide
4-Methyl-3-[(naphth-3-yl)ethynyl]benzohydrazide
4-Methyl-3-[5-tert-butyl-2-phenyl-2H-pyrazol-3-ylethynyl]benzohydrazide
4-Methyl-3-[(6-chloro-3-quinolin-3-yl)ethynyl]benzohydrazide
4-Methyl-3-[(6-fluoro-3-quinolin-3-yl)ethynyl]benzohydrazide
4-Methyl-3-[(2-quinolin-3-yl)ethynyl]benzohydrazide Reference Example 4

N'-(3-iodo-4-methylbenzoyl)-2,4,6-trichlorobenzohydrazide

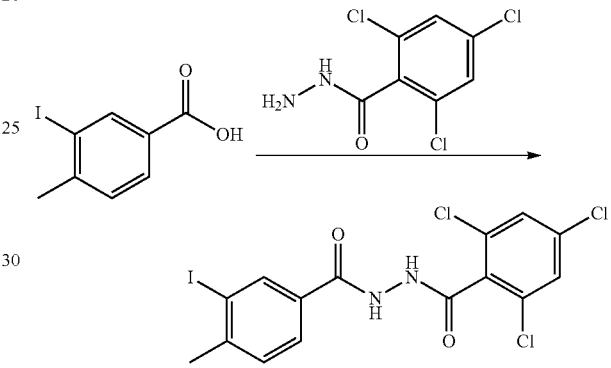

N-(3-iodo-4-methylbenzoyl)-2,4,6-trichlorobenzohydrazide was prepared by the reaction of 3-iodo-4-methylbenzoic acid with 2,4,6-trichlorobenzohydrazide. The coupling was performed in a manner similar to that described in Reference Example 3.

Similarly were prepared the following compounds from the appropriate acid compounds and the hydrazides:
N'-(2-Chloro-6-methylbenzoyl)-3-iodo-4-methylbenzohydrazide
3-Iodo-4-methyl-N'-[4-[(4-methylpiperazin-1-yl)methyl]-3-(trifluoromethyl)benzoyl]benzohydrazide
3-Iodo-N'-(2-iodo-6-methylbenzoyl)-4-methylbenzohydrazide
N'-(2,6-Dichlorobenzoyl)-3-iodo-4-methylbenzohydrazide
N'-[2,6-Bis(trifluoromethyl)benzoyl]-3-iodo-4-methylbenzohydrazide
3-Iodo-4-methyl-N'-[3-(4-methylimidazol-1-yl)-5-(trifluoromethyl)benzoyl]benzohydrazide
N'-(3-Iodo-4-methylbenzoyl)-2,4,6-trimethylbenzohydrazide
N'-(2-Bromo-6-methylbenzoyl)-3-iodo-4-methylbenzohydrazide
3-Iodo-N'-(2-methoxy-6-methylbenzoyl)-4-methylbenzohydrazide
N'-(2-Fluoro-6-methylbenzoyl)-3-iodo-4-methylbenzohydrazide
N'-(2-Chloro-6-methylbenzoyl)-4-fluoro-3-iodobenzohydrazide
N'-(2-Chloro-6-methylbenzoyl)-3-iodo-4-methoxybenzohydrazide
N'-(2-Fluoro-6-iodobenzoyl)-3-iodo-4-methylbenzohydrazide N'-[2-Chloro-6-(trifluoromethyl)benzoyl]-3-iodo-4-methyl-benzohydrazide N'-[2-Fluoro-6-(trifluoromethyl)benzoyl]-3-iodo-4-methyl-benzohydrazide N-tert-butyl-N'-(2-Chloro-6-methylbenzoyl)-3-iodo-4-methylbenzohydrazide N-Methyl-N'-(2-Chloro-6-methylbenzoyl)-3-iodo-4-methylbenzohydrazide Reference Example 5

Methyl 6-bromo-2-pyridinecarboxylate

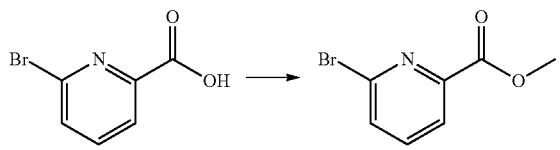

A mixture of 6-bromo-2-pyridinecarboxylic acid (0.3 g, 1.5 mmol), thionyl chloride (0.27 ml, 3.7 mmol) and DMF (catalytic amount) in methanol (10 ml) was heated to reflux for 2 hrs under nitrogen atmosphere. The reaction mixture was concentrated to dryness to provide methyl 6-bromo-2-pyridinecarboxylate.

$^1$H NMR (500 MHz in DMSO-$d_6$), δ3.95 (s, 3H), 7.85 (m, 1H), 8.01 (m, 1H), 8.12 (m, 1H).

Similarly were prepared the following ester compounds from their corresponding iodo esters:
Methyl 5-ethynyl-2-thiophenecarboxylate
Methyl 3-ethynyl-4-pyrazolecarboxylate
Methyl 2-ethynyl-5-thiazolecarboxylate Reference Example 6

6-[(Quinolin-3-yl)ethynyl]pyridine-2-carboxylic acid

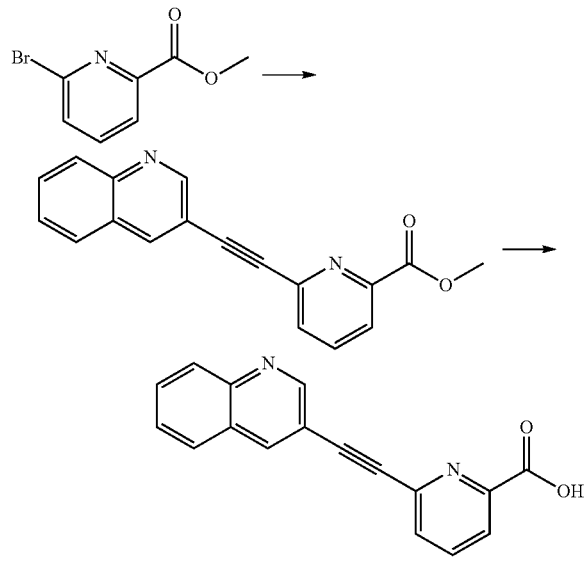

A mixture of methyl 6-bromo-2-pyridinecarboxylate (0.3 g, 1.3 mmol), 3-ethynylquinoline (0.3 g, 1.3 mmol), Pd(PPh$_3$)$_4$ (0.11 g, 0.01 mmol), CuI (0.179 g, 0.1 mmol) and diisopropylethylamine (0.5 ml, 3 mmol) in DMF (15 ml) was stirred at ambient temperature for 12 hrs under an atmosphere of nitrogen. The reaction mixture was concentrated and the crude product was purified by flash chromatography on silica gel (elution with 10% ethyl acetate in n-hexane) to provide methyl 6-[(quinolin-3-yl)ethynyl]pyridine-2-carboxylate.

Sodium hydroxide (0.15 g, 3.71 mmol) was added to a solution of the above methyl ester in methanol (20 ml) and water (3 ml) and stirred at 50° C. for 3 hrs and then concentrated in vacuo. Water (10 ml) was added to the residue, adjusted pH to 4.0-4.5 with citric acid. The solid obtained was filtered, washed successively with water and diethyl ether and dried at ambient temperature to obtain 6-[(quinolin-3-yl)ethynyl]pyridine-2-carboxylic acid.

$^1$H NMR (500 MHz in DMSO-$d_6$), δ 3.85 (s, 3H), 7.75 (t, $J_1$=15.1 Hz, $J_2$=8.2 Hz, 1H), 7.89 (t, $J_1$=13.7 Hz, $J_2$=8.5 Hz, 1H), 8.09 (d, J=8.2 Hz, 1H), 8.12-8.20 (m, 4H), 8.75 (s, 1H), 9.11 (s, 1H).

Similarly were prepared the following acid compounds from their corresponding halo esters:
5-[(Quinolin-3-yl)ethynyl]thiophene-2-carboxylic acid
3-[(Quinolin-3-yl)ethynyl]pyrazole-4-carboxylic acid
2-[(Quinolin-3-yl)ethynyl]thiazole-5-carboxylic acid Reference Example 7

4-Methyl-3-[(quinolin-3-yl)ethynyl]thiobenzoic acid

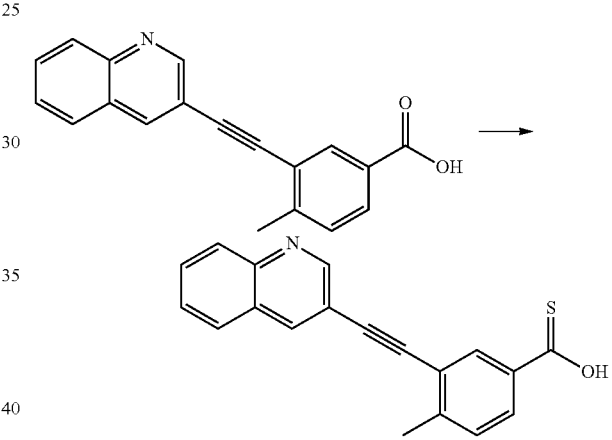

A mixture of 4-methyl-3-[(quinolin-3-yl)ethynyl]benzoic acid (0.3 g, 1.3 mmol) and Lawesson's reagent (0.5 ml, 1.3 mmol) in THF (10 ml) was stirred at ambient temperature for 1 hr under an atmosphere of nitrogen. The reaction mixture was concentrated and the crude product was purified by flash chromatography on silica gel (elution with 10% ethyl acetate in n-hexane) to provide 4-methyl-3-[(quinolin-3-yl)ethynyl]thiobenzoic acid.

Example I.1

2,4,6-Trichloro-N'-[4-methyl-3-[2-(3-quinolyl)ethynyl]benzoyl]benzohydrazide

Method A

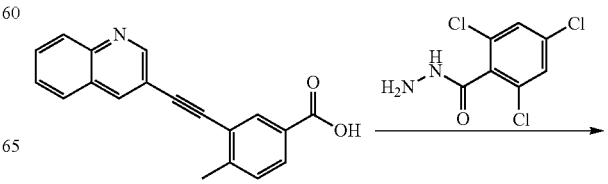

-continued

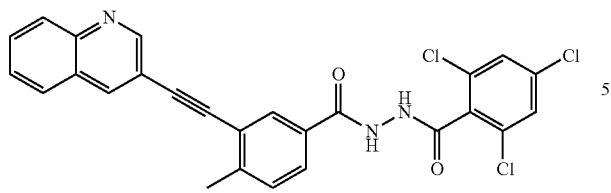

A mixture of 4-methyl-3-[(quinolin-3-yl)ethynyl]benzoic acid (0.15 g, 0.5 mmol), N-(3-dimethylaminopropyl)-N'-ethylcarbodiimide hydrochloride (0.15 g, 0.7 mmol) and 1-hydroxybenzotriazole (0.1 g, 0.7 mmol) in N,N-dimethylformamide (15 ml) was stirred at ambient temperature for 1 hr. 2,4,6-Trichlorobenzohydrazide (0.125 g, 0.5 mmol) was added and the mixture stirred for 12 hrs at ambient temperature. Concentration and trituration of the residue with water produced a solid which was filtered, washed with water and the crude product was purified by flash chromatography on silica gel (elution with 10% methanol in dichloromethane) to get 2,4,6-trichloro-N-[4-methyl-3-[2-(3-quinolyl)ethynyl]benzoyl]benzohydrazide as a white solid.

Method B 2,4,6-Trichloro-N'-[4-methyl-3-[2-(3-quinolyl)ethynyl]benzoyl]benzohydrazide was also prepared by the reaction of 4-methyl-3-[(quinolin-3-yl)ethynyl]benzoic acid with 2,4,6-trichlorobenzohydrazide in diethyl cyanophosphonate. The condensation reaction was performed in a manner similar to that described in Method A.

Method C

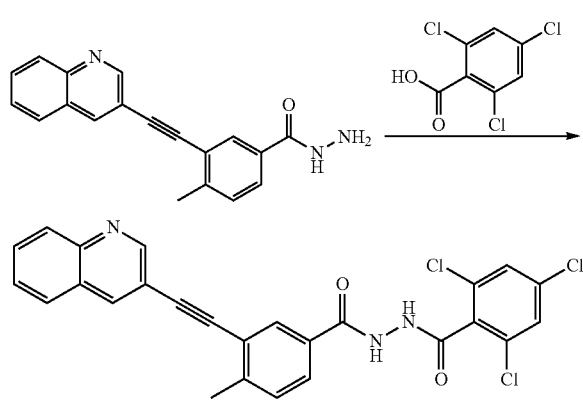

2,4,6-Trichloro-N-[4-methyl-3-[2-(3-quinolyl)ethynyl]benzoyl]benzohydrazide was also prepared by the reaction of 4-methyl-3-[(quinolin-3-yl)ethynyl]benzohydrazide with 2,4,6-trichlorobenzoyl chloride. The condensation reaction was performed in a manner similar to that described in Method A.

The compounds I.2 to I.14, I.21 to I.34, I.36 to I.40, and I.43 to I.59 were prepared in a manner similar to Example I.1, by following either of the methods A, B or C, using the appropriate substrates.

Example I.15

2,4,6-Trichloro-N'-[3-[2-(2-imidazo[1,2-a]pyrazin-3-yl)ethynyl)]]-4-methylbenzoyl]benzohydrazide

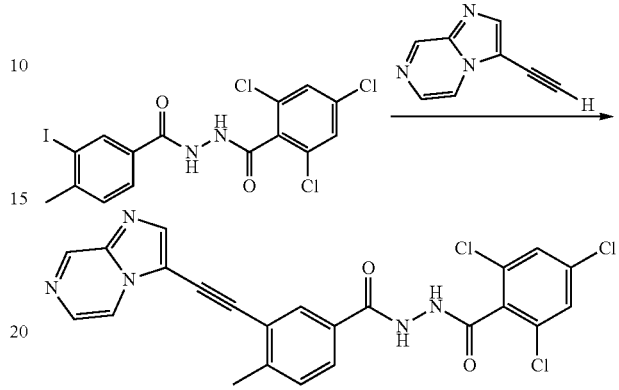

A mixture of 3-ethynylimidazo[1,2-a]pyrazine (0.09 g, 0.6 mmol), N'-(3-iodo-4-methylbenzoyl)-2,4,6-trichlorobenzohydrazide (0.3 g, 0.6 mmol), Pd(PPh$_3$)$_4$ (0.036 g, 0.03 mmol), CuI (0.008 g, 0.03 mmol) and diisopropylethylamine (0.75 ml, 0.9 mmol) in DMF (10 ml) was stirred at ambient temperature for 12 hrs under an atmosphere of nitrogen. The reaction mixture was concentrated and the crude product was purified by flash chromatography on silica gel (elution with 10% methanol in dichloromethane) to provide 2,4,6-trichloro-N'-[3-[2-(2-imidazo[1,2-a]pyrazin-3-yl)ethynyl)]]-4-methylbenzoyl]benzohydrazide.

The compounds I.16 to I.20, I.35, and I.41-I.42 were prepared in an analogous manner using the appropriate alkynes.

Example I.60

N'-(2-Chloro-6-methylbenzoyl)-6-[2-(3-quinolyl)ethynyl]pyridine-2-carboxylic acid hydrazide

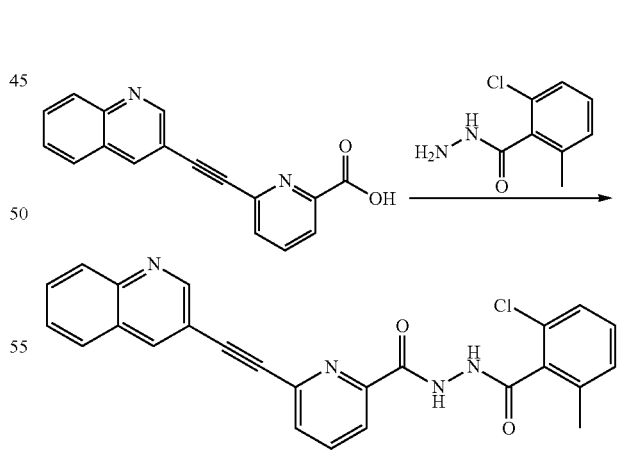

A mixture of 6-[(quinolin-3-yl)ethynyl]pyridine-2-carboxylic acid (0.05 g, 0.2 mmol), N-(3-dimethylaminopropyl)-N'-ethylcarbodiimide hydrochloride (0.04 g, 0.2 mmol) and 1-hydroxybenzotriazole (0.03 g, 0.2 mmol) in N,N-dimethylformamide (10 ml) was stirred at ambient temperature for 1 hr. 2-chloro-6-methylbenzohydrazide (0.03 g, 0.2 mmol) was added and the mixture stirred for 12 hrs at ambient temperature. Concentration and trituration of the residue with water produced a solid which was filtered, washed with water and dried in vacuo. Leaching the product with methanol and drying in vacuo gave N'-(2-Chloro-6-methylbenzoyl)-6-[2-(3-quinolyl)ethynyl]pyridine-2-carboxylic acid hydrazide as a white solid.

The compounds I.61 to I.63 were also prepared in a manner similar to Example I.60, by following either of the methods A, B or C, using the appropriate heterocyclic substrates.

Example I.64

2-Chloro-6-methyl-N'-[4-methyl-3-[2-(3-quinolyl) ethynyl]benzoyl]thiobenzohydrazide

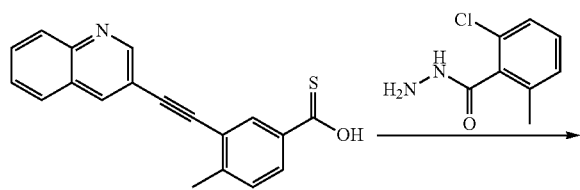

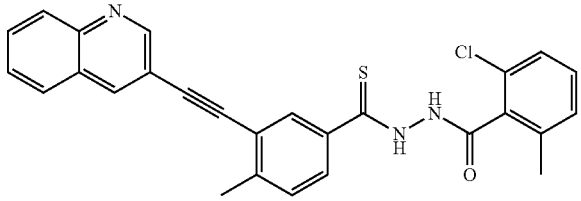

A mixture of 4-methyl-3-[(quinolin-3-yl)ethynyl]thiobenzoic acid (0.15 g, 0.5 mmol), N-(3-dimethylaminopropyl)-N'-ethylcarbodiimide hydrochloride (0.15 g, 0.7 mmol) and 1-hydroxybenzotriazole (0.1 g, 0.7 mmol) in N,N-dimethylformamide (15 ml) was stirred at ambient temperature for 1 hr. 2-Chloro-6-methylbenzohydrazide (0.125 g, 0.5 mmol) was added and the mixture stirred for 12 hrs at ambient temperature. Concentration and trituration of the residue with water produced a solid which was filtered, washed with water and finally purified by flash chromatography on silica gel (elution with 10% methanol in dichloromethane) to get 2-chloro-6-methyl-N-[4-methyl-3-[2-(3-quinolyl)ethynyl] thiobenzoyl]benzohydrazide as a white solid.

Table 1 below illustrates the chemical structures of compounds of formula (I),

TABLE 1

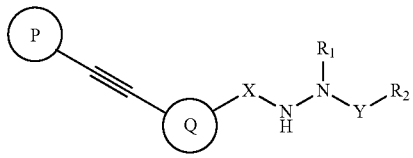

Formula (I)

| No. | P | Q | X | R₁ | Y | R₂ |
|---|---|---|---|---|---|---|
| I.1 | 3-Quinolinyl | 4-methyl-1,3-phenylene | C=O | H | C=O | 2,4,6-trichlorophenyl |
| I.2 | 3-Quinolinyl | 4-methyl-1,3-phenylene | C=O | H | C=O | 2-chloro-6-methylphenyl |
| I.3 | 3-Quinolinyl | 4-methyl-1,3-phenylene | C=O | H | C=O | 2-trifluoromethyl-4-[(4-methylpiperazin-1-yl)methyl]phenyl |
| I.4 | 3-Quinolinyl | 4-methyl-1,3-phenylene | C=O | H | C=O | 2-methyl-6-iodophenyl |

TABLE 1-continued

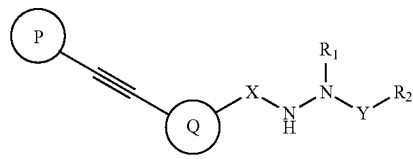

Formula (I)

| No. | P | Q | X | R₁ | Y | R₂ |
|---|---|---|---|---|---|---|
| I.5 | 3-Quinolinyl | 2-methyl-1,4-phenylene | C=O | H | C=O | 2,6-dichlorophenyl |
| I.6 | 3-Quinolinyl | 2-methyl-1,4-phenylene | C=O | H | C=O | 2,6-bis(trifluoromethyl)phenyl |
| I.7 | 3-Quinolinyl | 2-methyl-1,4-phenylene | C=O | H | C=O | 3-(4-methylimidazol-1-yl)-5-(trifluoromethyl)phenyl |
| I.8 | 3-Quinolinyl | 2-methyl-1,4-phenylene | C=O | H | C=O | 2,4,6-trimethylphenyl |
| I.9 | 3-Pyridinyl | 2-methyl-1,4-phenylene | C=O | H | C=O | 2-chloro-6-methylphenyl |
| I.10 | 6-Quinolinyl | 2-methyl-1,4-phenylene | C=O | H | C=O | 2-chloro-6-methylphenyl |
| I.11 | 3-Quinolinyl | 2-methyl-1,4-phenylene | C=O | H | C=O | 2-bromo-6-methylphenyl |

TABLE 1-continued

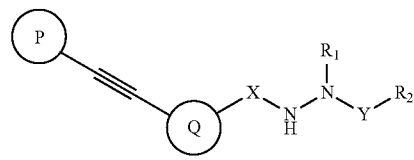

Formula (I)

| No. | P | Q | X | R₁ | Y | R₂ |
|---|---|---|---|---|---|---|
| I.12 | 2-Benzothiazolyl | 2-methyl-1,4-phenylene | C=O | H | C=O | 2-methyl-3-bromophenyl |
| I.13 | 3-Quinolinyl | 2-methyl-1,4-phenylene | C=O | H | C=O | 2-methyl-6-methoxyphenyl |
| I.14 | 3-Quinolinyl | 2-methyl-1,4-phenylene | C=O | H | C=O | 2-methyl-6-fluorophenyl |
| I.15 | Imidazo[1,2-a]pyrazinyl | 2-methyl-1,4-phenylene | C=O | H | C=O | 2,4,6-trichlorophenyl |
| I.16 | Imidazo[1,2-a]pyridazinyl | 2-methyl-1,4-phenylene | C=O | H | C=O | 2-methyl-6-chlorophenyl |
| I.17 | Imidazo[1,2-a]pyrazinyl | 2-methyl-1,4-phenylene | C=O | H | C=O | 2-methyl-6-chlorophenyl |
| I.18 | 3-Pyrimidinyl | 2-methyl-1,4-phenylene | C=O | H | C=O | 2-methyl-6-chlorophenyl |
| I.19 | Imidazo[1,2-a]pyridinyl | 2-methyl-1,4-phenylene | C=O | H | C=O | 2-methyl-6-chlorophenyl |

TABLE 1-continued

Formula (I)

| No. | P | Q | X | R₁ | Y | R₂ |
|---|---|---|---|---|---|---|
| I.20 | 2-Pyrazinyl | 2-methyl-1,4-phenylene | C=O | H | C=O | 2-methyl-6-chlorophenyl |
| I.21 | 3-Quinolinyl | 2-fluoro-1,4-phenylene | C=O | H | C=O | 2-methyl-6-chlorophenyl |
| I.22 | 3-Quinolinyl | 2-methoxy-1,4-phenylene | C=O | H | C=O | 2-methyl-6-chlorophenyl |
| I.23 | 3-Quinolinyl | 2-methyl-1,4-phenylene | C=O | H | C=O | 2-fluoro-6-chlorophenyl |
| I.24 | 3-Quinolinyl | 2-methyl-1,4-phenylene | C=O | H | C=O | 2-trifluoromethyl-6-chlorophenyl |
| I.25 | 3-Quinolinyl | 2-methyl-1,4-phenylene | C=O | H | C=O | 2-trifluoromethyl-6-fluorophenyl |
| I.26 | 7-Chloro-3-quinazolinyl | 2-methyl-1,4-phenylene | C=O | H | C=O | 2-methyl-6-chlorophenyl |
| I.27 | 3-quinazolinyl | 2-methyl-1,4-phenylene | C=O | H | C=O | 2-methyl-6-chlorophenyl |

TABLE 1-continued
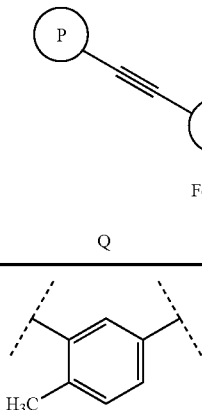
Formula (I)
| No. | P | Q | X | R₁ | Y | R₂ |
|---|---|---|---|---|---|---|
| I.28 | 3-Quinolinyl | 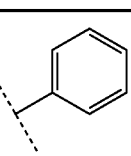 | C=O | H | C=O | 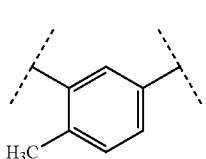 |
| I.29 | 3-Quinolinyl | 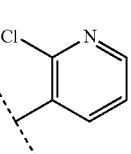 | C=O | H | C=O | 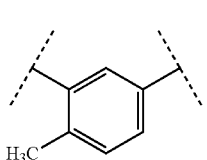 |
| I.30 | 3-Quinolinyl | 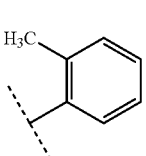 | C=O | H | C=O | 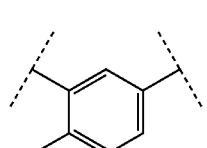 |
| I.31 | 3-Quinolinyl | 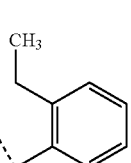 | C=O | H | C=O | 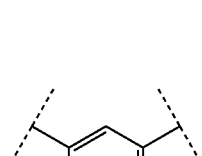 |
| I.32 | 3-Quinolinyl | 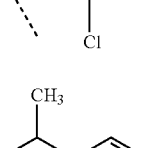 | C=O | H | C=O | 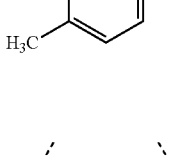 |
| I.33 | 3-Quinolinyl | 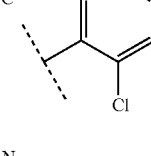 | C=O | H | C=O | 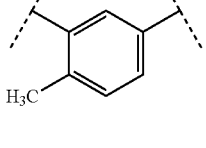 |
| I.34 | 3-Quinolinyl | 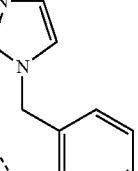 | C=O | H | C=O | (CH₃O, Cl substituted phenyl) |

TABLE 1-continued
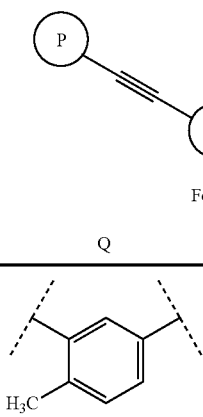
Formula (I)
| No. | P | Q | X | R₁ | Y | R₂ |
|---|---|---|---|---|---|---|
| I.35 | Pyrazolo[1,5-a]pyrimidinyl | 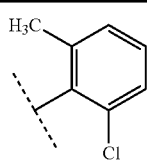 | C=O | H | C=O | 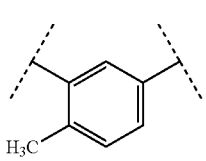 |
| I.36 | 3-Quinolinyl | 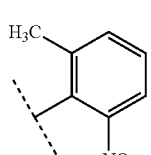 | C=O | H | C=O | 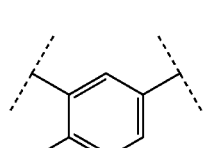 |
| I.37 | 3-Quinolinyl | 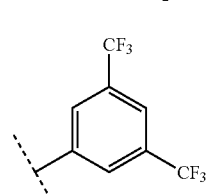 | C=O | H | C=O | 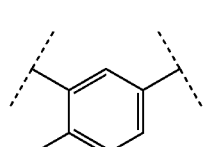 |
| I.38 | Pyrido[2,3-b]pyrazinyl | 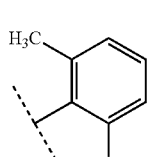 | C=O | H | C=O | 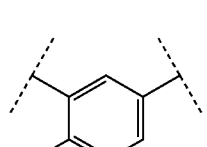 |
| I.39 | 3-Quinolinyl | 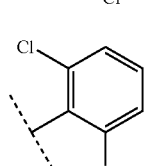 | C=O | H | C=O | 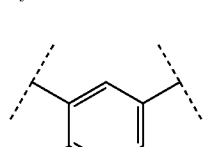 |
| I.40 | 3-Quinolinyl | 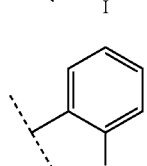 | C=O | H | C=O | 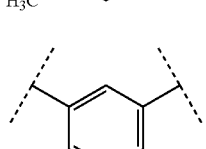 |
| I.41 | Imidazo[1,2-b]pyridazinyl | 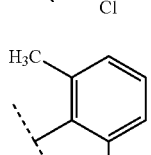 | C=O | H | C=O | 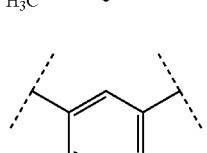 |
| I.42 | Imidazo[1,2-a]pyridinyl | 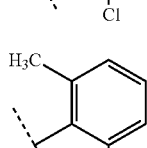 | C=O | H | C=O | |

TABLE 1-continued

Formula (I)

| No. | P | Q | X | R₁ | Y | R₂ |
|---|---|---|---|---|---|---|
| I.43 | 3-Quinolinyl | 2-methyl-1,4-phenylene | C=O | ᵗBu | C=O | 2-methyl-6-chlorophenyl |
| I.44 | 6-Methyl-3-quinolinyl | 2-methyl-1,4-phenylene | C=O | H | C=O | 2-methyl-6-chlorophenyl |
| I.45 | 3-Quinolinyl | 2-methyl-1,4-phenylene | C=O | CH₃ | C=O | 2-methyl-6-chlorophenyl |
| I.46 | 3-Quinolinyl | 2-methyl-1,4-phenylene | C=O | H | C=O | 2,6-dimethylphenyl |
| I.47 | 3-Quinolinyl | 2-methyl-1,4-phenylene | C=O | H | C=O | 3-trifluoromethyl-4-chlorophenyl |
| I.48 | 3-Naphthyl | 2-methyl-1,4-phenylene | C=O | H | C=O | 2-methyl-6-chlorophenyl |
| I.49 | 5-t-butyl-2-phenyl-2H-pyrazolyl | 2-methyl-1,4-phenylene | C=O | H | C=O | 2-methyl-6-chlorophenyl |
| I.50 | 6-Chloro-3-quinolinyl | 2-methyl-1,4-phenylene | C=O | H | C=O | 2-methyl-6-chlorophenyl |

TABLE 1-continued
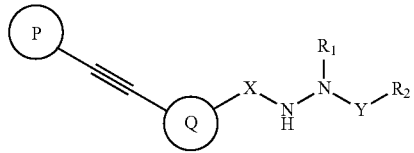
Formula (I)
| No. | P | Q | X | R₁ | Y | R₂ |
|---|---|---|---|---|---|---|
| I.51 | 3-Quinolinyl | 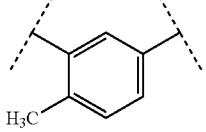 | C=O | H | C=O | 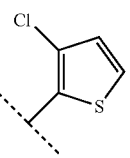 |
| I.52 | 3-Quinolinyl | 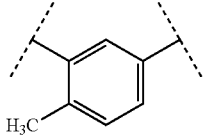 | C=O | H | C=O | 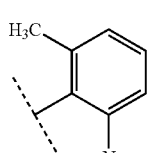 |
| I.53 | 3-Quinolinyl | 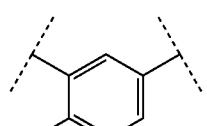 | C=O | H | C=O | 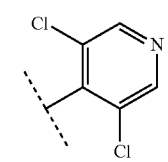 |
| I.54 | 3-Quinolinyl | 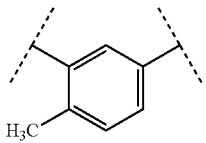 | C=O | H | C=O | 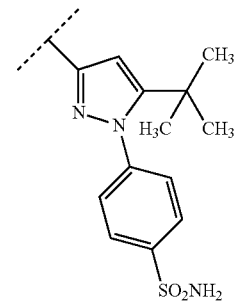 |
| I.55 | 6-Fluoro-3-quinolinyl | 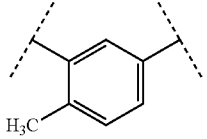 | C=O | H | C=O | 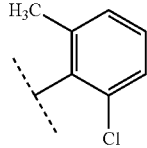 |
| I.56 | 2-quinolinyl | 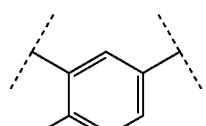 | C=O | H | C=O | 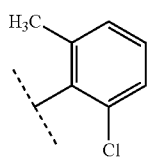 |
| I.57 | 3-Quinolinyl | 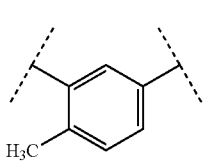 | C=O | H | C=O | 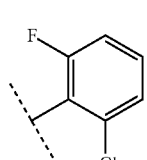 |

TABLE 1-continued

Formula (I)

| No. | P | Q | X | R$_1$ | Y | R$_2$ |
|---|---|---|---|---|---|---|
| I.58 | 3-Quinolinyl | 2-methyl-1,4-phenylene | C=O | H | C=O | 2-chloro-6-methylpyridin-3-yl |
| I.59 | 3-Quinolinyl | 1,3-phenylene | C=O | H | C=O | 2-chloro-6-methylphenyl |
| I.60 | 3-Quinolinyl | pyridine-2,6-diyl | C=O | H | C=O | 2-chloro-6-methylphenyl |
| I.61 | 3-Quinolinyl | thiophene-2,5-diyl | C=O | H | C=O | 2-chloro-6-methylphenyl |
| I.62 | 3-Quinolinyl | 1H-pyrazole-3,4-diyl | C=O | H | C=O | 2-chloro-6-methylphenyl |
| I.63 | 3-Quinolinyl | thiazole-2,5-diyl | C=O | H | C=O | 2-chloro-6-methylphenyl |
| I.64 | 3-Quinolinyl | 2-methyl-1,4-phenylene | C=S | H | C=O | 2-chloro-6-methylphenyl |

The spectral data for the compounds of formula (I) is provided in Table 2.

TABLE 2

| Compd. No. | $^1$H NMR (δ ppm) |
|---|---|
| I.1 | 2.67 (s, 3H), 7.59 (d, 1H, J = 8.0 Hz), 7.75 (t, 1H, J$_1$ = 14.8 Hz, J$_2$ = 7.2 Hz), 7.86 (s, 2H), 7.90 (t, 1H, J$_1$ = 15.1 Hz, J$_2$ = 7.5 Hz), 7.97 (d, 1H, J = |

TABLE 2-continued

| Compd. No. | $^1$H NMR ($\delta$ ppm) |
|---|---|
| | 7.5 Hz), 8.12 (t, 2H, $J_1$ = 17.9 Hz, $J_2$ = 8.9 Hz), 8.26 (s, 1H), 8.75 (s, 1H), 9.11 (s, 1H), 10.89 (s, 2H). |
| I.2 | 2.53 (s, 3H), 2.67 (s, 3H), 7.32-7.34 (m, 1H), 7.39-7.41 (m, 2H), 7.59 (d, 1H, J = 8.0 Hz), 7.75 (t, 1H, $J_1$ = 14.7 Hz, $J_2$ = 7.3 Hz), 7.90 (t, 1H, $J_1$ = 14.3 Hz, $J_2$ = 7.0 Hz), 7.98 (d, 1H, J = 7.9 Hz), 8.12 (t, 2H, $J_1$ = 18.0 Hz, $J_2$ = 8.9 Hz), 8.27 (s, 1H), 8.75 (s, 1H), 9.11 (s, 1H), 10.54 (s, 1H), 10.72 (s, 1H). |
| I.3 | 2.40 (s, 3H), 2.68 (m, 8H), 3.77 (s, 2H), 7.60 (d, 1H, J = 8.1 Hz), 7.75 (t, 1H, $J_1$ = 15.2 Hz, $J_2$ = 7.7 Hz), 7.89 (t, 1H, $J_1$ = 16.3 Hz, $J_2$ = 8.1 Hz), 7.98 (t, 2H, $J_1$ = 18.1 Hz, $J_2$ = 9.1 Hz), 8.12 (t, 2H, $J_1$ = 15.8 Hz, $J_2$ = 8.2 Hz), 8.23 (s, 1H), 8.27 (d, 1H, J = 8.2 Hz), 8.31 (s, 1H), 8.75 (s, 1H), 9.11 (s, 1H), 10.75 (s, 1H), 10.87 (s, 1H). |
| I.4 | 2.67 (s, 3H), 7.14 (t, 1H, $J_1$ = 15.4 Hz, $J_2$ = 7.7 Hz), 7.36 (d, 1H, J = 7.7 Hz), 7.59 (d, 1H, J = 8.1 Hz), 7.74-7.77 (m, 2H), 7.90 (t, 1H, $J_1$ = 16.3 Hz, $J_2$ = 8.2 Hz), 7.99 (d, 1H, J = 7.9 Hz), 8.12 (t, 2H, $J_1$ = 17.6 Hz, $J_2$ = 8.8 Hz), 8.29 (s, 1H), 8.75 (s, 1H), 9.11 (d, 1H, J = 1.9 Hz), 10.47 (s, 1H), 10.74 (s, 1H). |
| I.5 | 2.68 (s, 3H), 7.53-7.62 (m, 4H), 7.75 (t, 1H, $J_1$ = 15.0 Hz, $J_2$ = 7.5 Hz), 7.89 (t, 1H, $J_1$ = 15.1 Hz, $J_2$ = 7.7 Hz), 7.98 (d, 1H, J = 7.8 Hz), 8.12 (t, 2H, $J_1$ = 15.6 Hz, $J_2$ = 8.0 Hz), 8.27 (s, 1H), 8.75 (s, 1H), 9.11 (s, 1H), 10.84 (s, 1H), 10.85 (s, 1H). |
| I.6 | 2.67 (s, 3H), 7.59 (d, 1H, J = 8.0 Hz), 7.76 (t, 1H, $J_1$ = 15.0 Hz, $J_2$ = 7.6 Hz), 7.90 (t, 1H, $J_1$ = 15.2 Hz, $J_2$ = 7.7 Hz), 7.97-7.99 (m, 2H), 8.12 (t, 2H, $J_1$ = 14.8 Hz, $J_2$ = 7.6 Hz), 8.23 (d, 2H, J = 8.0 Hz), 8.29 (s, 1H), 8.76 (s, 1H), 9.12 (s, 1H), 10.88 (s, 1H), 10.95 (s, 1H). |
| I.7 | 2.25 (s, 3H), 2.68 (s, 3H), 7.62 (d, 1H, J = 8.1 Hz), 7.73-7.77 (m, 2H), 7.90 (t, 1H, $J_1$ = 15.0 Hz, $J_2$ = 8.0 Hz), 7.98 (d, 1H, J = 7.9 Hz), 8.12 (t, 2H, $J_1$ = 15.4 Hz, $J_2$ = 7.9 Hz), 8.23 (d, 2H, J = 9.4 Hz), 8.35 (s, 1H), 8.46 (d, 2H, J = 8.0 Hz), 8.76 (s, 1H), 9.12 (s, 1H), 10.87 (s, 1H), 10.98 (s, 1H). |
| I.8 | 2.31 (s, 3H), 2.38 (s, 6H), 2.67 (s, 3H), 6.95 (s, 2H), 7.60 (d, 1H, J = 8.1 Hz), 7.75 (t, 1H, $J_1$ = 15.0 Hz, $J_2$ = 7.7 Hz), 7.90 (t, 1H, $J_1$ = 15.2 Hz, $J_2$ = 7.7 Hz), 7.97 (d, 1H, J = 7.7 Hz), 8.12 (t, 2H, $J_1$ = 15.5 Hz, $J_2$ = 8.0 Hz), 8.25 (s, 1H), 8.75 (s, 1H), 9.12 (s, 1H), 10.22 (s, 1H), 10.60 (s, 1H). |
| I.9 | 2.29 (s, 3H), 2.52 (s, 3H), 7.31-7.35 (m, 2H), 7.41 (d, 1H, J = 8.3 Hz), 7.45-7.47 (m, 1H), 7.52-7.55 (m, 1H), 7.87 (d, 1H, J = 8.1 Hz), 8.07 (d, 1H, J = 7.8 Hz), 8.16 (s, 1H), 8.65 (m, 1H), 8.84 (s, 1H), 10.68 (s, 1H), 10.98 (s, 1H). |
| I.10 | 2.53 (s, 3H), 2.66 (s, 3H), 7.32-7.34 (m, 1H), 7.39-7.43 (m, 2H), 7.58 (d, 1H, J = 8.0 Hz), 7.65-7.68 (m, 1H), 7.96 (d, 2H, J = 8.4 Hz), 8.13 (d, 1H, J = 8.7 Hz), 8.24 (m, 1H), 8.37 (m, 1H), 8.49 (d, 1H, J = 8.0 Hz), 9.00 (m, 1H), 10.54 (s, 1H), 10.74 (s, 1H). |
| I.11 | 2.67 (s, 3H), 7.31-7.37 (m, 2H), 7.55 (d, 1H, J = 7.2 Hz), 7.59 (d, 1H, J = 8.0 Hz), 7.75 (t, 1H, $J_1$ = 15.0 Hz, $J_2$ = 7.5 Hz), 7.90 (t, 1H, $J_1$ = 15.2 Hz, $J_2$ = 7.6 Hz), 7.98 (d, 1H, J = 7.7 Hz), 8.12 (t, 2H, $J_1$ = 15.6 Hz, $J_2$ = 8.0 Hz), 8.28 (s, 1H), 8.75 (s, 1H), 9.11 (s, 1H), 10.53 (s, 1H), 10.75 (s, 1H). |
| I.12 | 2.53 (s, 3H), 2.65 (s, 3H), 7.32-7.34 (m, 1H), 7.39-7.42 (m, 2H), 7.61-7.68 (m, 3H), 8.04-8.07 (m, 1H), 8.17 (d, 1H, J = 7.9 Hz), 8.25 (d, 1H, J = 7.7 Hz), 8.34 (m, 1H), 10.57 (s, 1H), 10.78 (s, 1H). |
| I.13 | 2.46 (s, 3H), 2.66 (s, 3H), 3.82 (s, 3H), 6.91 (d, 1H, J = 7.4 Hz), 6.97 (d, 1H, J = 8.3 Hz), 7.34 (t, 1H, $J_1$ = 15.8 Hz, $J_2$ = 7.9 Hz), 7.58 (d, 1H, J = 8.1 Hz), 7.76 (t, 1H, $J_1$ = 15.0 Hz, $J_2$ = 7.5 Hz), 7.90 (t, 1H, $J_1$ = 15.1 Hz, $J_2$ = 7.6 Hz), 7.98 (d, 1H, J = 8.0 Hz), 8.12 (t, 2H, t, 1H, $J_1$ = 17.9 Hz, $J_2$ = 9.0 Hz), 8.26 (s, 1H), 8.75 (s, 1H), 9.11 (s, 1H), 10.22 (s, 1H), 10.68 (s, 1H). |
| I.14 | 2.51 (s, 3H), 2.67 (s, 3H), 7.15-7.21 (m, 2H), 7.42-7.47 (m, 1H), 7.59 (d, 1H, J = 8.1 Hz), 7.76 (t, 1H, $J_1$ = 14.6 Hz, $J_2$ = 7.2 Hz), 7.90 (t, 1H, $J_1$ = 14.4 Hz, $J_2$ = 6.9 Hz), 7.98 (d, 1H, J = 7.9 Hz), 8.12 (t, 2H, t, 1H, $J_1$ = 18.4 Hz, $J_2$ = 9.1 Hz), 8.25 (s, 1H), 8.75 (s, 1H), 9.11 (s, 1H), 10.53 (s, 1H), 10.74 (s, 1H). |
| I.15 | 2.67 (s, 3H), 7.60 (d, 1H, J = 8.0 Hz), 7.86 (s, 2H), 7.98 (d, 1H, J = 7.8 Hz), 8.20 (d, 1H, J = 4.2 Hz), 8.32-8.33 (m, 2H), 8.75 (d, 1H, J = 3.7 Hz), 9.27 (s, 1H), 10.88 (s, 2H). |
| I.16 | 2.53 (s, 3H), 2.66 (s, 3H), 7.32-7.33 (m, 1H), 7.39-7.41 (m, 2H), 7.44-7.46 (m, 1H), 7.59 (d, 1H, J = 8.1 Hz), 7.97 (d, 1H, J = 8.0 Hz), 8.23 (s, 1H), 8.29 (s, 1H), 8.32 (d, 1H, J = 9.2 Hz), 8.78 (d, 1H, J = 4.2 Hz), 10.53 (s, 1H), 10.75 (s, 1H). |
| I.17 | 2.53 (s, 3H), 2.67 (s, 3H), 7.32-7.34 (m, 1H), 7.40-7.42 (m, 2H), 7.60 (d, 1H, J = 8.1 Hz), 7.99 (d, 1H, J = 7.9 Hz), 8.21 (d, 1H, J = 4.3 Hz), 8.34 (s, 2H), 8.75 (d, 1H, J = 3.6 Hz), 9.28 (s, 1H), 10.55 (s, 1H), 10.74 (s, 1H). |
| I.18 | 2.52 (s, 3H), 2.63 (s, 3H), 7.31-7.33 (m, 1H), 7.40-7.41 (m, 2H), 7.58 (d, 1H, J = 8.1 Hz), 7.99 (d, 1H, J = 9.0 Hz), 8.23 (s, 1H), 9.13 (s, 2H), 9.28 (s, 1H), 10.53 (s, 1H), 10.74 (s, 1H). |
| I.19 | 2.53 (s, 3H), 2.66 (s, 3H), 7.25 (t, 1H, $J_1$ = 13.5 Hz, $J_2$ = 6.8 Hz), 7.32-7.35 (m, 1H), 7.39-7.42 (m, 2H), 7.52 (t, 1H, $J_1$ = 15.6 Hz, $J_2$ = 8.3 Hz), 7.58 (d, 1H, J = 8.1 Hz), 7.81 (d, 1H, J = 9.0 Hz), 7.96 (d, 1H, J = 7.9 Hz), 8.13 (s, 1H), 8.29 (s, 1H), 8.68 (d, 1H, J = 6.6 Hz), 10.54 (s, 1H), 10.73 (s, 1H). |
| I.20 | 2.52 (s, 3H), 2.64 (s, 3H), 7.31-7.35 (m, 1H), 7.38-7.41 (m, 2H), 7.60 (d, 1H, J = 8.0 Hz), 8.00-8.02 (m, 1H), 8.28 (m, 1H), 8.73 (m, 1H), 8.78 (m, 1H), 9.01 (m, 1H), 10.54 (s, 1H), 10.75 (s, 1H). |

TABLE 2-continued

| Compd. No. | $^1$H NMR ($\delta$ ppm) |
|---|---|
| I.21 | 2.53 (s, 3H), 7.32-7.35 (m, 1H), 7.40-7.44 (m, 2H), 7.63 (t, 1H, J = 8.9 Hz), 7.76 (t, 1H, J = 7.5 Hz), 7.91 (t, 1H, J = 7.3 Hz), 8.11-8.16 (m, 3H), 8.39-8.41 (m, 1H), 8.79 (s, 1H), 9.10 (m, 1H), 10.60 (s, 1H), 10.84 (s, 1H). |
| I.22 | 2.53 (s, 3H), 4.05 (s, 3H), 7.33-7.37 (m, 2H), 7.40-7.43 (m, 2H), 7.75 (t, 1H, J = 7.4 Hz), 7.89 (t, 1H, J = 7.4 Hz), 8.10-8.13 (m, 3H), 8.29 (m, 1H), 8.70 (s, 1H), 9.06 (m, 1H), 10.51 (s, 1H), 10.66 (s, 1H). |
| I.23 | 2.67 (s, 3H), 7.32-7.35 (m, 1H), 7.40-7.44 (m, 1H), 7.58-7.64 (m, 1H), 7.73-7.77 (m, 1H), 7.81 (d, 1H, J = 7.7 Hz), 7.87-7.91 (m, 1H), 7.98 (d, 1H, J = 7.8 Hz), 8.10-8.14 (m, 2H), 8.27 (s, 1H), 8.76 (s, 1H), 9.11 (m, 1H), 10.77 (s, 1H), 10.86 (s, 1H). |
| I.24 | 2.67 (s, 3H), 7.59 (d, 1H, J = 8.0 Hz), 7.74-7.78 (m, 2H), 7.87-7.91 (m, 2H), 7.95-7.99 (m, 2H), 8.10-8.14 (m, 2H), 8.28 (s, 1H), 8.76 (s, 1H), 9.11 (m, 1H), 10.86 (s, 1H), 10.88 (s, 1H). |
| I.25 | 2.67 (s, 3H), 7.59 (d, 1H, J = 7.5 Hz), 7.76-7.87 (m, 4H), 7.89-7.98 (m, 2H), 8.10-8.13 (m, 2H), 8.26 (s, 1H), 8.75 (s, 1H), 9.11 (m, 1H), 10.87 (s, 2H). |
| I.26 | 2.53 (s, 3H), 2.70 (s, 3H), 7.32-7.34 (m, 1H), 7.40-7.42 (m, 2H), 7.63 (d, 1H, J = 8.1 Hz), 8.02-8.06 (m, 2H), 8.21 (d, 1H, J = 9.0 Hz), 8.31 (d, 1H, J = 2.3 Hz), 8.37 (s, 1H), 9.27 (s, 1H), 10.56 (s, 1H), 10.78 (s, 1H). |
| I.27 | 2.53 (s, 3H), 2.70 (s, 3H), 7.32-7.34 (m, 1H), 7.40-7.42 (m, 2H), 7.63 (d, 1H, J = 8.1 Hz), 7.96-8.05 (m, 3H), 8.17-8.21 (m, 2H), 8.37 (d, 1H, J = 1.8 Hz), 9.24 (s, 1H), 10.56 (s, 1H), 10.78 (s, 1H). |
| I.28 | 2.66 (s, 3H), 7.45-7.48 (m, 1H), 7.56-7.60 (m, 2H), 7.73-7.77 (m, 2H), 7.87-7.90 (m, 1H), 7.96 (d, 1H, J = 8.0 Hz), 8.03 (d, 1H, J = 8.4 Hz), 8.08-8.13 (m, 3H), 8.17 (s, 1H), 8.75 (s, 1H), 9.11 (s, 1H), 13.52 (m, 2H). |
| I.29 | 2.67 (s, 3H), 7.60 (d, 1H, J = 8.1 Hz), 7.63-7.65 (m, 1H), 7.74-7.77 (m, 1H), 7.88-7.91 (m, 1H), 7.96-7.98 (d, 1H, J = 7.9 Hz), 8.05 (d, 1H, J = 7.5 Hz), 8.12 (dd, 2H, $J_1$ = 17.9 Hz, $J_2$ = 9.0 Hz), 8.24 (s, 1H), 8.60-8.62 (m, 1H), 8.75 (s, 1H), 9.12 (s, 1H), 10.78 (m, 2H). |
| I.30 | 2.50 (s, 3H), 2.67 (s, 3H), 7.33-7.37 (m, 2H), 7.45 (t, 1H, $J_1$ = 14.6 Hz, $J_2$ = 7.3 Hz), 7.51 (d, 1H, J = 7.2 Hz), 7.59 (d, 1H, J = 7.9 Hz), 7.75 (t, 1H, $J_1$ = 14.7 Hz, $J_2$ = 7.4 Hz), 7.90 (t, 1H, $J_1$ = 15.0 Hz, $J_2$ = 7.4 Hz), 7.97 (d, 1H, J = 7.7 Hz), 8.12 (t, 2H, $J_1$ = 18.0 Hz, $J_2$ = 9.0 Hz), 8.24 (s, 1H), 8.75 (s, 1H), 9.12 (s, 1H), 10.28 (s, 1H), 10.66 (s, 1H). |
| I.31 | 1.27 (t, 3H, $J_1$ = 15.0 Hz, $J_2$ = 7.5 Hz), 2.67 (s, 3H), 2.87-2.91 (m, 2H), 7.36-7.47 (m, 3H), 7.59 (d, 1H, J = 8.1 Hz), 7.76 (t, 1H, $J_1$ = 15.9 Hz, $J_2$ = 7.9 Hz), 7.88-7.91 (m, 1H), 7.98 (d, 1H, J = 8.1 Hz), 8.12 (t, 2H, $J_1$ = 17.9 Hz, $J_2$ = 8.9 Hz), 8.27 (s, 1H), 8.75 (s, 1H), 9.12 (s, 1H), 10.52 (s, 1H), 10.73 (s, 1H). |
| I.32 | 1.29 (s, 6H), 2.67 (s, 3H), 3.45-3.51 (m, 1H), 7.39-7.41 (m, 1H), 7.46-7.50 (m, 2H), 7.59 (d, 1H, J = 8.0 Hz), 7.76 (t, 1H, $J_1$ = 15.0 Hz, $J_2$ = 7.6 Hz), 7.90 (t, 1H, $J_1$ = 15.1 Hz, $J_2$ = 7.7 Hz), 7.99 (d, 1H, J = 7.9 Hz), 8.12 (t, 2H, $J_1$ = 18.0 Hz, $J_2$ = 9.0 Hz), 8.28 (s, 1H), 8.75 (s, 1H), 9.12 (s, 1H), 10.52 (s, 1H), 10.72 (s, 1H). |
| I.33 | 2.48 (s, 3H), 5.47 (s, 2H), 6.89 (s, 1H), 7.23 (d, 1H, J = 7.5 Hz), 7.27 (s, 1H), 7.44-7.54 (m, 3H), 7.67 (t, 1H, $J_1$ = 15.0 Hz, $J_2$ = 7.6 Hz), 7.81-7.84 (m, 2H), 7.93 (d, 1H, J = 7.9 Hz), 8.04 (t, 2H, $J_1$ = 19.0 Hz, $J_2$ = 9.3 Hz), 8.21 (s, 1H), 8.68 (s, 1H), 9.04 (s, 1H), 10.79 (m, 2H). |
| I.34 | 2.67 (s, 3H), 3.88 (s, 3H), 7.14-7.16 (m, 2H), 7.48 (t, 1H, $J_1$ = 16.5 Hz, $J_2$ = 8.2 Hz), 7.58 (d, 1H, J = 8.1 Hz), 7.76 (t, 1H, $J_1$ = 14.6 Hz, $J_2$ = 7.2 Hz), 7.90 (t, 1H, $J_1$ = 16.3 Hz, $J_2$ = 8.0 Hz), 7.98 (d, 1H, J = 8.1 Hz), 8.12 (t, 2H, $J_1$ = 17.9 Hz, $J_2$ = 9.0 Hz), 8.26 (s, 1H), 8.75 (s, 1H), 9.11 (s, 1H), 10.51 (s, 1H), 10.76 (s, 1H). |
| I.35 | 2.52 (s, 3H), 2.64 (s, 3H), 6.90 (s, 1H), 7.33 (d, 1H, J = 5.5 Hz), 7.40-7.41 (m, 2H), 7.58 (d, 1H, J = 8.0 Hz), 7.97 (d, 1H, J = 7.9 Hz), 8.22 (s, 1H), 8.40 (s, 1H), 8.78 (s, 1H), 9.64 (s, 1H), 10.53 (s, 1H), 10.74 (s, 1H). |
| I.36 | 2.55 (s, 3H), 2.59 (s, 3H), 7.51 (d, 1H, J = 8.1 Hz), 7.58 (t, 1H, $J_1$ = 15.8 Hz, $J_2$ = 7.9 Hz), 7.68 (t, 1H, $J_1$ = 14.8 Hz, $J_2$ = 7.5 Hz), 7.72 (d, 1H, J = 7.6 Hz), 7.83 (t, 1H, $J_1$ = 16.1 Hz, $J_2$ = 8.1 Hz), 7.91 (d, 1H, J = 7.9 Hz), 7.98 (d, 1H, J = 8.1 Hz), 8.04 (t, 2H, $J_1$ = 17.0 Hz, $J_2$ = 8.6 Hz), 8.21 (s, 1H), 8.67 (s, 1H), 9.03 (s, 1H), 10.53 (s, 1H), 10.72 (s, 1H). |
| I.37 | 2.68 (s, 3H), 7.61 (d, 1H, J = 7.5 Hz), 7.75 (t, 1H, $J_1$ = 14.4 Hz, $J_2$ = 7.3 Hz), 7.90 (t, 1H, $J_1$ = 14.6 Hz, $J_2$ = 7.4 Hz), 7.97 (d, 1H, J = 7.5 Hz), 8.12 (t, 2H, $J_1$ = 17.0 Hz, $J_2$ = 8.6 Hz), 8.24 (s, 1H), 8.50 (s, 1H), 8.64 (s, 2H), 8.76 (s, 1H), 9.12 (s, 1H), 10.89 (s, 1H), 11.18 (s, 1H). |
| I.38 | 2.53 (s, 3H), 2.69 (s, 3H), 7.32-7.33 (m, 1H), 7.39-7.43 (m, 2H), 7.61 (d, 1H, J = 8.1 Hz), 8.01 (d, 1H, J = 7.9 Hz), 8.31 (s, 1H), 8.86 (d, 1H, J = 2.2 Hz), 9.19 (s, 1H), 9.21 (s, 1H), 9.40 (d, 1H, J = 2.1 Hz), 10.54 (s, 1H), 10.75 (s, 1H). |
| I.39 | 2.67 (s, 3H), 7.25 (t, 1H, $J_1$ = 16.0 Hz, $J_2$ = 8.0 Hz), 7.58-7.63 (m, 2H), 7.75 (t, 1H, $J_1$ = 15.3 Hz, $J_2$ = 7.5 Hz), 7.90 (t, 1H, $J_1$ = 16.5 Hz, $J_2$ = 8.1 Hz), 7.94 (d, 1H, J = 7.8 Hz), 7.99 (d, 1H, J = 8.0 Hz), 8.12 (t, 2H, $J_1$ = 17.4 Hz, $J_2$ = 8.7 Hz), 8.29 (s, 1H), 8.75 (s, 1H), 9.11 (s, 1H), 10.79 (s, 1H), 10.86 (s, 1H). |
| I.40 | 2.67 (s, 3H), 7.53-7.63 (m, 5H), 7.75 (t, 1H, $J_1$ = 14.9 Hz, $J_2$ = 7.5 Hz), 7.90 (t, 1H, $J_1$ = 16.1 Hz, $J_2$ = 8.1 Hz), 7.97 (d, 1H, J = 7.9 Hz), 8.12 (t, 2H, $J_1$ = 17.9 Hz, $J_2$ = 8.9 Hz), 8.24 (s, 1H), 8.75 (s, 1H), 9.11 (s, 1H), 10.52 (s, 1H), 10.77 (s, 1H). |

TABLE 2-continued

| Compd. No. | $^1$H NMR ($\delta$ ppm) |
|---|---|
| I.41 | 2.65 (s, 3H), 7.42-7.71 (m, 5H), 7.97 (d, 1H, J = 8.2 Hz), 8.23-8.34 (m, 3H), 8.79 (d, 1H, J = 3.2 Hz), 10.85 (s, 2H). |
| I.42 | 2.54 (s, 3H), 2.69 (s, 3H), 6.99 (t, 1H, $J_1$ = 13.1 Hz, $J_2$ = 6.6 Hz), 7.33-7.40 (m, 4H), 7.51 (d, 1H, J = 7.8 Hz), 7.68 (d, 1H, J = 8.1 Hz), 7.87 (d, 1H, J = 7.6 Hz), 8.38 (s, 1H), 8.63-8.65 (m, 2H), 10.49 (s, 1H), 10.70 (s, 1H). |
| I.43 | 1.60 (s, 9H), 2.37 (s, 3H), 2.57 (s, 3H), 7.12 (d, 1H, J = 7.7 Hz), 7.20-7.23 (m, 1H), 7.35-7.44 (m, 3H), 7.58 (s, 1H), 7.75 (t, 1H, $J_1$ = 15.2 Hz, $J_2$ = 7.7 Hz), 7.90 (t, 1H, $J_1$ = 15.3 Hz, $J_2$ = 7.9 Hz), 8.12-8.13 (m, 2H), 8.71 (s, 1H), 9.08 (s, 1H), 10.53 (s, 1H). |
| I.44 | 2.66 (s, 3H), 7.33 (s, 1H), 7.40 (m, 2H), 7.59 (s, 1H), 7.73 (s, 1H), 7.86 (s, 1H), 7.98-8.01 (m, 2H), 8.26 (m, 1H), 8.62 (m, 1H), 9.03 (s, 1H), 10.54 (s, 1H), 10.74 (s, 1H). |
| I.45 | 2.36 (s, 3H), 2.58 (s, 3H), 3.36 (s, 3H), 7.20-7.29 (m, 2H), 7.32-7.35 (m, 1H), 7.42-7.53 (m, 2H), 7.72-7.78 (m, 2H), 7.86-7.91 (m, 1H), 8.12 (t, 2H, $J_1$ = 13.5 Hz, $J_2$ = 6.7 Hz), 8.72 (s, 1H), 9.07 (s, 1H), 10.80 (s, 1H). |
| I.46 | 2.43 (s, 6H), 2.68 (s, 3H), 7.14 (d, 2H, J = 7.6 Hz), 7.28 (t, 1H, $J_1$ = 15.2 Hz, $J_2$ = 7.6 Hz), 7.60 (d, 1H, J = 8.0 Hz), 7.76 (t, 1H, $J_1$ = 14.7 Hz, $J_2$ = 7.6 Hz), 7.90 (t, 1H, $J_1$ = 16.1 Hz, $J_2$ = 7.9 Hz), 7.97 (d, 1H, J = 7.9 Hz), 8.12 (t, 2H, $J_1$ = 17.8 Hz, $J_2$ = 8.9 Hz), 8.26 (s, 1H), 8.75 (s, 1H), 9.11 (s, 1H), 10.30 (s, 1H), 10.62 (s, 1H). |
| I.47 | 2.68 (s, 3H), 7.60 (d, 1H, J = 8.0 Hz), 7.74-7.77 (m, 1H), 7.88-7.91 (m, 1H), 7.96 (d, 1H, J = 7.5 Hz), 8.01 (d, 1H, J = 8.3 Hz), 8.10-8.13 (m, 2H), 8.22 (s, 1H), 8.29 (d, 1H, J = 8.1 Hz), 8.43 (s, 1H), 8.76 (s, 1H), 9.11 (m, 1H), 10.80 (s, 1H), 10.96 (s, 1H). |
| I.48 | 2.53 (s, 3H), 2.66 (s, 3H), 7.32-7.33 (m, 1H), 7.40-7.43 (m, 2H), 7.57 (d, 1H, J = 7.9 Hz), 7.64-7.65 (m, 2H), 7.72 (d, 1H, J = 8.4 Hz), 7.95 (d, 1H, J = 7.9 Hz), 8.04-8.06 (m, 3H), 8.23 (s, 1H), 8.30 (s, 1H), 10.53 (s, 1H), 10.73 (s, 1H). |
| I.49 | 1.39 (s, 9H), 2.43 (s, 3H), 2.52 (s, 3H), 6.95 (s, 1H), 7.19 (s, 1H), 7.40 (s, 2H), 7.50-7.56 (m, 2H), 7.60-7.63 (m, 2H), 7.85 (d, 2H, J = 7.4 Hz), 7.95 (d, 1H, J = 7.4 Hz), 8.11 (s, 1H), 10.53 (s, 1H), 10.72 (s, 1H). |
| I.50 | 2.53 (s, 3H), 2.67 (s, 3H), 7.32-7.35 (m, 1H), 7.39-7.43 (m, 2H), 7.60 (d, 1H, J = 8.1 Hz), 7.89 (dd, 1H, $J_1$ = 9.1 Hz, $J_2$ = 2.3 Hz), 7.99 (dd, 1H, $J_1$ = 8.0 Hz, $J_2$ = 1.5 Hz), 8.15 (d, 1H, J = 8.9 Hz), 8.24 (d, 1H, J = 2.2 Hz), 8.27 (s, 1H), 8.72 (s, 1H), 9.13 (s, 1H), 10.54 (s, 1H), 10.78 (s, 1H). |
| I.51 | 2.67 (s, 3H), 7.28 (d, 1H, J = 5.2 Hz), 7.60 (d, 1H, J = 8.1 Hz), 7.75 (t, 1H, $J_1$ = 15.2 Hz, $J_2$ = 7.9 Hz), 7.89 (t, 1H, $J_1$ = 16.5 Hz, $J_2$ = 8.6 Hz), 7.95 (d, 1H, J = 7.9 Hz), 7.98 (d, 1H, J = 5.2 Hz), 8.12 (t, 2H, $J_1$ = 17.6 Hz, $J_2$ = 8.8 Hz), 8.21 (s, 1H), 8.76 (s, 1H), 9.11 (s, 1H), 10.33 (s, 1H), 10.74 (s, 1H). |
| I.52 | 2.48 (s, 3H), 2.67 (s, 3H), 7.18 (d, 1H, J = 7.6 Hz), 7.29 (d, 1H, J = 8.1 Hz), 7.48 (t, 1H, $J_1$ = 15.8 Hz, $J_2$ = 7.9 Hz), 7.59 (d, 1H, J = 8.0 Hz), 7.76 (t, 1H, $J_1$ = 15.0 Hz, $J_2$ = 7.6 Hz), 7.90 (t, 1H, $J_1$ = 15.0 Hz, $J_2$ = 7.3 Hz), 7.98 (d, 1H, J = 7.9 Hz), 8.12 (t, 2H, $J_1$ = 18.2 Hz, $J_2$ = 9.2 Hz), 8.26 (s, 1H), 8.75 (s, 1H), 9.11 (s, 1H), 10.38 (s, 1H), 10.73 (s, 1H). |
| I.53 | 2.67 (s, 3H), 7.60 (d, 1H, J = 8.1 Hz), 7.75 (t, 1H, $J_1$ = 16.1 Hz, $J_2$ = 8.1 Hz), 7.87-7.91 (m, 1H), 7.96-8.00 (m, 1H), 8.12 (t, 2H, $J_1$ = 15.3 Hz, $J_2$ = 7.3 Hz), 8.26 (s, 1H), 8.75 (s, 1H), 8.83 (s, 2H), 9.11 (s, 1H), 11.00 (s, 1H), 11.08 (s, 1H). |
| I.54 | 1.25 (s, 9H), 2.66 (s, 3H), 6.84 (s, 1H), 7.58 (d, 1H, J = 8.2 Hz), 7.65 (s, 2H), 7.75 (t, 1H, $J_1$ = 15.4 Hz, $J_2$ = 7.6 Hz), 7.83 (d, 2H, J = 8.5 Hz), 7.89 (t, 1H, $J_1$ = 16.4 Hz, $J_2$ = 9.5 Hz), 7.94 (d, 1H, J = 8.0 Hz), 8.06 (d, 2H, J = 8.5 Hz), 8.11 (t, 2H, $J_1$ = 18.5 Hz, $J_2$ = 9.3 Hz), 8.20 (s, 1H), 8.75 (s, 1H), 9.11 (s, 1H), 10.24 (s, 1H), 10.54 (s, 1H). |
| I.55 | 2.67 (s, 3H), 7.37-7.40 (m, 3H), 7.60 (d, 1H, J = 7.3 Hz), 7.80 (m, 1H), 7.91 (d, 1H, J = 6.2 Hz), 7.99 (m, 1H), 8.19 (m, 1H), 8.27 (s, 1H), 8.73 (s, 1H), 9.10 (s, 1H), 10.55 (s, 1H), 10.75 (s, 1H). |
| I.56 | 2.68 (s, 3H), 7.33 (m, 1H), 7.40 (s, 2H), 7.61 (d, 1H, J = 7.6 Hz), 7.73 (m, 1H), 7.87 (t, 1H, $J_1$ = 20.8 Hz, $J_2$ = 8.4 Hz), 8.01 (d, 1H, J = 6.6 Hz), 8.10 (m, 2H), 8.32 (s, 1H), 8.53 (d, 1H, J = 7.7 Hz), 9.10 (s, 1H), 10.55 (s, 1H), 10.76 (s, 1H). |
| I.57 | 2.67 (s, 3H), 7.40-7.43 (m, 1H), 7.49 (d, 1H, J = 8.0 Hz), 7.58-7.63 (m, 2H), 7.74-7.77 (m, 1H), 7.88-7.91 (m, 1H), 7.97 (d, 1H, J = 7.1 Hz), 8.10-8.14 (m, 2H), 8.25 (s, 1H), 8.75 (s, 1H), 9.11 (m, 1H), 10.82 (s, 1H), 10.85 (s, 1H). |
| I.58 | 2.65 (s, 3H), 7.42 (d, 1H, J = 7.6 Hz), 7.52 (d, 1H, J = 7.7 Hz), 7.73-7.76 (m, 1H), 7.87-7.93 (m, 3H), 8.09-8.13 (m, 2H), 8.20 (s, 1H), 8.75 (s, 1H), 9.11 (s, 1H), 10.64 (s, 2H). |
| I.59 | 2.53 (s, 3H), 7.32-7.34 (m, 1H), 7.39-7.43 (m, 2H), 7.69-7.77 (m, 2H), 7.88-7.93 (m, 2H), 8.06-8.13 (m, 3H), 8.29 (s, 1H), 8.74 (m, 1H), 9.11 (m, 1H), 10.58 (s, 1H), 10.82 (s, 1H). |
| I.60 | 2.52 (s, 3H), 7.31-7.34 (m, 1H), 7.38-7.43 (m, 2H), 7.78 (t, 1H, $J_1$ = 15.3 Hz, $J_2$ = 7.4 Hz), 7.91-7.95 (m, 1H), 8.06 (d, 1H, J = 8.2 Hz), 8.13-8.23 (m, 4H), 8.82 (s, 1H), 9.15 (m, 1H), 10.64 (s, 1H), 10.84 (s, 1H). |
| I.61 | 2.44 (s, 3H), 7.25-7.27 (m, 1H), 7.32-7.36 (m, 2H), 7.58 dt, 1H, J = 3.9 Hz), 7.67-7.70 (m, 1H), 7.81-7.85 (m, 1H), 7.93 (d, 1H, J = 3.9 Hz), 8.01-8.06 (m, 2H), 8.70 (s, 1H), 9.01 (m, 1H), 10.53 (s, 1H), 10.84 (s, 1H). |

TABLE 2-continued

| Compd. No. | $^1$H NMR (δ ppm) |
|---|---|
| 1.62 | 2.53 (s, 3H), 7.32-7.33 (m, 1H), 7.39-7.41 (m, 2H), 7.73-7.76 (m, 1H), 7.88-7.91 (m, 1H), 8.08-8.13(m, 2H), 8.47 (s, 1H), 8.71 (s, 1H), 9.06 (m, 1H), 10.25 (s, 1H), 10.51 (s, 1H), 13.74 (s, 1H). |
| 1.63 | 2.55 (s, 3H), 7.08 (s, 1H), 7.33-7.34 (m, 1H), 7.41 (s, 1H), 7.75-7.78 (m, 1H), 7.90-7.93 (m, 1H), 8.14-8.19 (m, 2H), 8.59 (s, 1H), 8.76 (m, 1H), 9.25 (m, 1H), 10.60 (s, 1H), 10.87 (s, 1H). |

Pharmacological Activity
In-Vitro Cell Proliferation Assay

K562/U937 cells ($2\times10^4$ per well) were incubated with the test compounds/vehicle in a total volume of 200 μL of media at 37° C. with 5% $CO_2$. On day 4, 20 μL MTT 5 mg/ml was added and the cells were incubated for 4-5 hours followed by addition of 100 μL of 10% SDS prepared in 0.06N HCl. The cells were incubated overnight at 37° C. with 5% $CO_2$. On Day 5 the optical density was measured at 570 nm with 630 nm as reference wavelength. The optical density in the vehicle treated wells was compared with that of the test compound treated wells.

TABLE 3

Inhibition of cell proliferation in K562 cells (in vitro)

| Compound No. | % Inhibition | |
|---|---|---|
| | 10 nM | 100 nM |
| I.1 | 101.0 | 104.9 |
| I.3 | 14.6 | 73.4 |
| I.4 | 102.1 | 100.5 |
| I.5 | 99.8 | 99.9 |
| I.7 | 12.6 | 43.1 |
| I.8 | 53.6 | 80.3 |
| I.11 | 78.9 | 79.9 |
| I.13 | 52.2 | 73.5 |
| I.14 | 68.5 | 71.7 |
| I.15 | 82.8 | 85.0 |
| I.16 | 103.6 | 102.1 |
| I.18 | 11.6 | 69.5 |
| I.19 | 60.2 | 80.2 |
| I.21 | 40.9 | 98.6 |
| I.23 | 68.1 | 72.6 |
| I.24 | 71.1 | 71.3 |
| I.25 | 71.5 | 73.0 |
| I.26 | 71.8 | 78.2 |
| I.27 | 79.3 | 75.3 |
| I.29 | 27.7 | 78.5 |
| I.30 | 49.0 | 85.0 |
| I.31 | 74.2 | 81.4 |
| I.32 | 50.6 | 81.9 |
| I.34 | 75.5 | 82.2 |
| I.36 | 75.9 | 77.3 |
| I.39 | 77.1 | 80.5 |
| I.40 | 59.9 | 84.3 |
| I.41 | 82.5 | 81.1 |
| I.44 | 77.7 | 84.4 |
| I.45 | 10.2 | 78.2 |
| I.46 | 77.9 | 83.9 |
| I.50 | 69.6 | 75.0 |
| I.60 | 8.6 | 8.5 |
| Imatinib | 9.2 | 34.0 |

Compounds of formula (I) when similarly screened for cell proliferation using U937 cells however did not show any significant inhibition, indicating selectivity for only the Bcr-Abl bearing cells.

Kinase Assays

The kinase assays were performed by Millipore Pharma Services at their UK pharmacology laboratory.

Abl Kinase

In a final reaction volume of 25 μL, Abl (human) (5-10 mU) is incubated with 8 mM MOPS pH7.0, 0.2 mM EDTA, 50 μM EAIYAAPFAKKK, 10 mM Mg(OAc)$_2$ and [γ-$^{33}$P-ATP] [specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 75 mM phosphoric acid and once in methanol prior to drying and scintillation counting.

Mutated Abl Kinases

The procedure remains exactly the same as described earlier for Abl kinase, the Abl (human) kinase being replaced by mutated Abl (Q252H) (human), Abl (Y253F) (human), Abl (T315I) (human), Abl (M351T) (human) and Abl (H396P) (human) kinases.

Lck Kinases

In a final reaction volume of 25 μL, Lck (human) (5-10 mU) is incubated with 50 mM Tris pH 7.5, 0.1 mM EGTA, 0.1 mM Na$_3$VO$_4$, 250 μM KVEKIGEGTYGVVYK [Cdc2 peptide), 10 mM Mg(OAc)$_2$ and [γ-$^{33}$P-ATP] [specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 75 mM phosphoric acid and once in methanol prior to drying and scintillation counting.

Lyn Kinases

In a final reaction volume of 25 μL, Lyn (human) (5-10 mU) is incubated with 50 mM Tris pH 7.5, 0.1 mM EGTA, 0.1 mM Na$_3$VO$_4$, 0.1% β-mercaptoethanol, 0.1 mg/ml poly(Glu, tyr) 4:1, 10 mM Mg(OAc)$_2$ and [γ-$^{33}$P-ATP] [specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a filtermat A and washed three times for 5 minutes in 75 mM phosphoric acid and once in methanol prior to drying and scintillation counting.

Percent Inhibition Data Analysis

Within each kinase assay, percent of control values were calculated for each test compound raw data point based on mean minimum (0%) and maximum (100%) controls (n=4 per control) for that kinase (sample−mean minimum/mean maximum−mean minimum×100%). Percent inhibition was calculated from these values (100−mean percent of control).

TABLE 4

Abl-T315I kinase inhibition (in vitro)

| Compound No. | % Inhibition of Abl-T315I kinase | | | |
|---|---|---|---|---|
| | 3 nM | 30 nM | 100 nM | 1000 nM |
| I.4 | | | 90.0 | 100.0 |
| I.16 | | | 70.0 | 93.0 |
| I.5 | 30.0 | 83.0 | | |
| I.25 | 26.0 | 65.0 | | |
| I.14 | 1.0 | 60.0 | | |
| I.26 | 3.0 | 41.0 | | |
| I.27 | 0.0 | 55.0 | | |
| Imatinib | | | 0.0 | 0.0 |

TABLE 5

Mutated Abl kinases' inhibition (in vitro)

| Compound No. | % Inhibition at 100 nM | | | |
|---|---|---|---|---|
| | Q252H | Y253F | M351T | H396P |
| I.2 | 100.0 | 101.0 | 100.0 | 99.0 |
| I.4 | 100.0 | 98.0 | 99.0 | 100.0 |
| I.16 | 98.0 | 98.0 | 100.0 | 99.0 |

TABLE 6

Lck and Lyn kinase inhibition (in vitro)

| Compound No. | % Inhibition at 100 nM | |
|---|---|---|
| | Lck | Lyn |
| I.2 | 84.0 | 97.0 |
| I.4 | 81.0 | 97.0 |
| I.16 | 65.0 | 74.0 |
| Imatinib | — | 19.5 |

All publications and patent applications cited in this application are herein incorporated by reference to the same extent as if each individual publication or patent application was specifically and individually indicated to be incorporated herein by reference.

We claim:

1. A compound of formula (I),

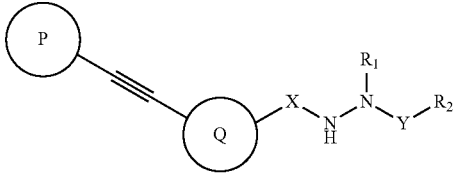

Formula (I)

or pharmaceutically acceptable salt thereof, wherein;
ring P is selected from a 5 to 14 membered heteroaryl ring containing one to four hetero atoms, each independently selected from O, S and N; and ring Q is selected from an aryl ring having 6 to 14 carbon atoms, or a 5 to 14 membered heteroaryl ring containing one to four hetero atoms each independently selected from O, S and N, wherein ring P and Q are optionally substituted by one or more identical or different radicals $R_3$;

$R_1$ and $R_2$ are independently selected from the group consisting of hydrogen, —$C_{1-8}$-alkyl, —$C_{2-10}$-alkenyl, —$C_{2-12}$-alkynyl, —$C_{3-12}$-cycloalkyl, —$C_{4-12}$-cycloalkylalkyl, —$C_{3-12}$-cycloalkenyl, aryl, heteroaryl, arylalkyl and a heteroarylalkyl radical, wherein the aryl ring contains 6 to 14 carbon atoms, and the heteroaryl ring contains 5 to 14 membered ring system with one to four hetero atoms each independently selected from O, S and N, and are optionally substituted by one or more identical or different radicals $R_3$;

X and Y are independently selected from the group consisting of C=O and C=S;

$R_3$ is selected from the group consisting of halogen, —OH, —CN, —$NO_2$, —$N_3$, —$C_{1-8}$-alkyl, —$C_{3-12}$-cycloalkyl, —($C_{1-8}$-alkyl)-$C_{3-12}$-cycloalkyl, -heterocycloalkyl containing 3 to 12 rings atoms having one or two hetero atoms each independently selected from O, S and N, —($C_{1-8}$-alkyl)-heterocycloalkyl containing 3 to 12 rings atoms having one or two hetero atoms each independently selected from O, S and N, —O—$C_{1-8}$-alkyl, —O—$C_{3-12}$-cycloalkyl, —O-aryl, —O-heteroaryl, —$C_{1-8}$ alkyl-O—$C_{1-8}$ alkyl, —O—$C_{1-8}$ alkyl-O—$C_{1-8}$ alkyl, —O—$C_{1-8}$ alkyl-NH($C_{1-8}$ alkyl), —O—$C_{1-8}$ alkyl-N($C_{1-8}$ alkyl)$_2$, —O—$C_{1-8}$ alkyl-(heteroaryl), —C(O)—$C_{1-8}$ alkyl, —COOH, —C(O)$NH_2$, —C(O)NH—$C_{1-8}$ alkyl, —C(O)N($C_{1-8}$ alkyl)$_2$, —C(O)O—$C_{1-8}$ alkyl, —$C_{1-8}$ haloalkyl, —$C_{2-10}$ alkenyl, —$C_{2-12}$ alkynyl, —OC(O)—$NH_2$, —OC(O)—NH($C_{1-8}$ alkyl), —OC(O)—N($C_{1-8}$ alkyl)$_2$, —$NH_2$, —NH($C_{1-8}$ alkyl), —N($C_{1-8}$ alkyl)$_2$, —NH—$SO_2$—$C_{1-8}$ alkyl, —N($C_{1-8}$ alkyl)-$SO_2$—$C_{1-8}$ alkyl, —NH—C(O)—($C_{1-8}$ alkyl), —N($C_{1-8}$ alkyl)-C(O)—($C_{1-8}$ alkyl), —NH—C(O)O—$C_{1-8}$ alkyl, —N($C_{1-8}$ alkyl)-C(O)O—$C_{1-8}$ alkyl, —NH—C(O)—$NH_2$, —NH—C(O)—NH($C_{1-8}$ alkyl), —N($C_{1-8}$ alkyl)-C(O)—NH($C_{1-8}$ alkyl), —N($C_{1-8}$ alkyl)-C(O)—N($C_{1-8}$ alkyl)$_2$, —NH—C(O)—NH—$SO_2$—$C_{1-8}$ alkyl, —N($C_{1-8}$ alkyl)-C(O)—$NHSO_2$—$C_{1-8}$ alkyl, —N($C_{1-8}$ alkyl)-C(O)—N($C_{1-8}$ alkyl)-$SO_2$—$C_{1-8}$ alkyl, —S—$C_{1-8}$ alkyl, —S(O)—$C_{1-8}$ alkyl, —$SO_2$—$C_{1-8}$ alkyl, —S-aryl, —S(O)-aryl, $SO_2$-aryl, —$SO_2NH_2$, —$SO_2$NH—($C_{1-8}$ alkyl), —$SO_2$N($C_{1-8}$ alkyl)$_2$; -aryl, —($C_{1-4}$-alkyl)-aryl, heteroaryl or —($C_{1-4}$-alkyl)-heteroaryl group, wherein the aryl ring contains 6 to 14 carbon atoms, and the heteroaryl ring contains 5 to 14 membered ring system with one to four hetero atoms each independently selected from O, S and N, wherein each of the aforementioned $R_3$ groups may be optionally substituted with a single group selected from the group consisting of: $C_{1-4}$-alkyl, $C_{1-4}$-alkoxy, $C_{1-4}$-haloalkyl, —OH, —COOH, —CN, —$NO_2$, halo, —$NH_2$ and —$SO_2NH_2$.

2. A compound according to claim 1, wherein ring P is selected from pyridine, thiophene, pyrazole, thiazole, quinoline, benzothiazole, pyrazine, pyrimidine, quinoxaline, quinazoline, imidazo[1,2-a]pyrazine, imidazo[1,2-a]pyridazine, imidazo[1,2-a]pyridine, pyrazolo[1,5-a]pyrimidine, pyrido[2,3-b]pyrazine, cinnoline, phthalazine, and ring Q is selected from phenyl, naphthyl, pyridine, thiophene, pyrazole, thiazole, quinoline, benzothiazole, pyrazine, pyrimidine, quinoxaline, quinazoline, imidazo[1,2-a]pyrazine, imidazo[1,2-a]pyridazine, imidazo[1,2-a]pyridine, pyrazolo[1,5-a]pyrimidine, pyrido[2,3-b]pyrazine, cinnoline, phthalazine, wherein ring P and ring Q are optionally substituted by one or more identical or different radicals $R_3$.

3. A compound according to claim 1, wherein $R_1$ is selected from hydrogen, —$C_{1-8}$-alkyl, —$C_{2-10}$-alkenyl, —$C_{2-12}$-alkynyl, —$C_{3-12}$-cycloalkyl, —$C_{4-12}$-cycloalkylalkyl or a —$C_{3-12}$-cycloalkenyl group.

4. A compound according to claim 1, wherein $R_2$ is selected from aryl, heteroaryl, arylalkyl or a heteroarylalkyl radical, wherein the aryl ring contains 6 to 14 carbon atoms, and the heteroaryl ring contains 5 to 14 membered ring system with one to four hetero atoms each independently selected from O, S and N, and are optionally substituted by one or more identical or different radicals $R_3$.

5. A compound according to claim 4 wherein $R_2$ is an aryl or a heteroaryl ring selected from phenyl, pyridine, thiophene or pyrazole, optionally substituted by one or more identical or different radicals $R_3$.

6. A compound according to claim 1 wherein both X and Y are C=O.

7. A compound according to claim 1 wherein X is C=S and Y is C=O.

8. A compound according to claim 1 wherein $R_3$ is selected from the group consisting of halogen, —OH, —CN, —$NO_2$, —$N_3$, —$C_{1-8}$-alkyl, —$C_{3-12}$-cycloalkyl, —O—$C_{1-8}$ alkyl, —O—$C_{3-12}$-cycloalkyl, —$C_{1-8}$-haloalkyl, —($C_{1-8}$-alkyl)-heterocyclo alkyl containing 3 to 12 rings atoms having one or two hetero atoms each independently selected from O, S and N, aryl group, heteroaryl group, or —($C_{1-4}$-alkyl)-heteroaryl group, wherein the aryl ring contains 6 to 14 carbon atoms, and the heteroaryl ring contains 5 to 14 membered ring system with one to four hetero atoms each independently selected from O, S and N; wherein each of the aforementioned $R_3$ groups may be optionally substituted with a single group selected from the group consisting of: $C_{1-4}$-alkyl, $C_{1-4}$-alkoxy, $C_{1-4}$-haloalkyl, —OH, —COOH, —CN, —$NO_2$, halo, —$NH_2$ and —$SO_2NH_2$.

9. A compound according to claim 1 wherein X and Y are C=O, $R_1$ is hydrogen, $R_2$, ring P is heteroaryl, and ring Q is aryl or heteroaryl.

10. A compound according to claim 1 selected from the group consisting of 2,4,6-Trichloro-N'-[4-methyl-3-[2-(3-quinolyl)ethynyl]benzoyl]benzohydrazide, N'-(2-Chloro-6-methylbenzoyl)-4-methyl-3-[2-(3-quinolyl)ethynyl]benzohydrazide, N'-(2-Iodo-6-methylbenzoyl)-4-methyl-3-[2-(3-quinolyl)ethynyl]benzohydrazide, N'-(2,6-Dichlorobenzoyl)-4-methyl-3-[2-(3-quinolyl)ethynyl]benzohydrazide, N'-(2-Fluoro-6-methylbenzoyl)-4-methyl-3-[2-(3-quinolyl)ethynyl]benzohydrazide, 2,4,6-Trichloro-N'-[3-[2-(2-imidazo[1,2-a]pyrazin-3-yl)ethynyl]-4-methylbenzoyl]benzohydrazide, N'-(2-Chloro-6-methylbenzoyl)-3-[2-(imidazo[1,2-b]pyridazin-3-yl)ethynyl]-4-methylbenzohydrazide, N'-(2-Chloro-6-methylbenzoyl)-3-[2-(imidazo[1,2-a]pyrazin-3-yl)ethynyl]-4-methylbenzohydrazide, N'-[2-Fluoro-6-(trifluoromethyl)benzoyl]-4-methyl-3-[2-(3-quinolyl)ethynyl]benzohydrazide, N'-(2-Chloro-6-methylbenzoyl)-4-methyl-3-[2-(quinoxalin-2-yl)ethynyl]benzohydrazide, N'-(2,6-Dichlorobenzoyl)-4-methyl-3-[(imidazo[1,2-b]pyridazin-3-yl)ethynyl]benzohydrazide, N'-(2-Chloro-6-methylbenzoyl)-4-methyl-3-[2-(6-fluoro-3-quinolyl)ethynyl]benzohydrazide, N'-(2-Chloro-6-fluorobenzoyl)-4-methyl-3-[2-(3-quinolyl)ethynyl]benzohydrazide, and a pharmaceutically acceptable salt thereof.

* * * * *